US008771754B2

(12) United States Patent
Hallahan

(10) Patent No.: US 8,771,754 B2
(45) Date of Patent: Jul. 8, 2014

(54) USE OF GSK3 INHIBITORS IN COMBINATION WITH RADIATION THERAPIES

(75) Inventor: Dennis E. Hallahan, Nashville, TN (US)

(73) Assignee: Vanderbilt University, Knoxville, TN (US)

( * ) Notice: Subject to any disclaimer, the term of this patent is extended or adjusted under 35 U.S.C. 154(b) by 1611 days.

(21) Appl. No.: 11/663,314

(22) PCT Filed: Sep. 19, 2005

(86) PCT No.: PCT/US2005/033504
§ 371 (c)(1),
(2), (4) Date: Sep. 10, 2008

(87) PCT Pub. No.: WO2006/034207
PCT Pub. Date: Mar. 30, 2006

(65) Prior Publication Data
US 2009/0041863 A1 Feb. 12, 2009

Related U.S. Application Data

(60) Provisional application No. 60/611,430, filed on Sep. 17, 2004.

(51) Int. Cl.
*A61K 33/14* (2006.01)

(52) U.S. Cl.
USPC .......................................................... 424/677

(58) Field of Classification Search
None
See application file for complete search history.

(56) References Cited

U.S. PATENT DOCUMENTS

| | | |
|---|---|---|
| 2001/0039275 A1 | 11/2001 | Bowler et al. |
| 2002/0147146 A1 | 10/2002 | Eldar-Finkelman |
| 2003/0130289 A1 | 7/2003 | Nuss et al. |
| 2003/0194745 A1 | 10/2003 | McDowell et al. |
| 2003/0195238 A1 | 10/2003 | Gil et al. |
| 2004/0006095 A1 | 1/2004 | Zhang et al. |
| 2004/0028656 A1 | 2/2004 | Willing et al. |
| 2004/0034037 A1 | 2/2004 | Harbeson et al. |
| 2004/0039007 A1 | 2/2004 | Forster et al. |
| 2004/0054180 A1 | 3/2004 | Zhang et al. |
| 2004/0077681 A1 | 4/2004 | Rawlings et al. |
| 2004/0077707 A1 | 4/2004 | Desai et al. |
| 2004/0106615 A1 | 6/2004 | Cochran et al. |
| 2004/0110837 A1 | 6/2004 | Phiel et al. |
| 2004/0138273 A1 | 7/2004 | Wagman et al. |
| 2004/0162234 A1 | 8/2004 | Eldar-Finkelman et al. |

FOREIGN PATENT DOCUMENTS

| | | | |
|---|---|---|---|
| WO | WO 01/47533 | * | 7/2001 |
| WO | WO 03/088954 A1 | * | 10/2003 |
| WO | WO 2004/016211 A1 | * | 2/2004 |

OTHER PUBLICATIONS

Jordan et al. Cancer Res., 2002, vol. 62, pp. 3555-3561.*
Hager et al. Biological Trace Element Research, 2001, vol. 83, pp. 139-148.*
Lyman et al. N. Engl. J. Med., 1980, vol. 302, pp. 257-260.*
Beauchesne et al. Am. J. Clin. Oncol., 2003, vol. 26, No. 3, pp. e22-e27.*
Hastrup. Acta Radiologica, 1961, vol. 56, pp. 124-128.*
Lyman et al. The American Journal of Medicine, 1981, vol. 70, No. 6, pp. 1222-1229.*
Cohen et al. Nature Reviews, Jun. 2004, vol. 3, pp. 479-487.*
Phiel et al. Annu. Rev. Pharmcol. Toxicol., 2001, vol. 41, pp. 789-813.*
International Preliminary Report on Patentability corresponding to a PCT Application No. PCT/US2005/033504 dated Mar. 20, 2007.
Written Opinion of the International Searching Authority corresponding to a PCT Application No. PCT/US2005/033504 dated Aug. 28, 2006.
International Search Report corresponding to a PCT Application No. PCT/US2005/033504 dated Aug. 28, 2006.
Nikoulina et al. Inhibition of glycogen synthase kinase 3 improves insulin action and glucose metabolism in human skeletal muscle. *Diabetes*, vol. 51, (2002), pp. 2190-2198.
Ohira et al. WNT7a induces E-cadherin in lung cancer cells. *Proceedings of the National Academy of Sciences of USA*, vol. 100, No. 18, (2003), pp. 10429-10434.
G-Amlak et al. Regulation of myeloma cell growth through Akt/Gsk3/forkhead signaling pathway. *Biochemical and Biophysical Research Communications*, vol. 297, (2002), pp. 760-764.
Brambilla et al., "1H MRS Study of Dorsolateral Prefrontal Cortex in Healthy Individuals Before and After Lithium Administration", Neuropsychopharmacology, vol. 29, pp. 1918-1924 (2004).
Chen, R. and Chuang, D., "Long Term Lithium Treatment Suppresses p53 and Bax Expression but Increases Bcl-2-Expression. A Prominent Role in Neuroprotection Against Excitotoxicity", Journal of Biological Chemistry, vol. 274, No. 10, pp. 6039-6042 (1999).
Edwards et al., "Phosphatidylinositol 3-kinase/Akt Signaling in the Response of Vascular Endothelium to Ionizing Radiation", Cancer Research, vol. 62, pp. 4671-4677 (2002).
Garcia-Barros et al., "Tumor Response to Radiotherapy Regulated by Endothelial Cell Apoptosis", Science, vol. 300, pp. 1155-1159 (2003).

(Continued)

*Primary Examiner* — James D Anderson
(74) *Attorney, Agent, or Firm* — Jenkins, Wilson, Taylor & Hunt, P.A.

(57) ABSTRACT

The presently disclosed subject matter relates generally to the fields of molecular biology and medicine. More particularly, it concerns methods involving the use of GSK3 inhibitors in combination with radiation therapies. In some embodiments, administration of a GSK3 inhibitor to a subject results in an amelioration of cognitive decline, toxicity to vascular endothelial cells, and/or neuron death associated with radiation therapy alone.

35 Claims, 19 Drawing Sheets

(56) References Cited

OTHER PUBLICATIONS

Geng et al., "Inhibition of Vascular Endothelial Growth Factor Receptor Signaling Leads to Reversal of Tumor Resistance to Radiotherapy", Cancer Research, vol. 61, pp. 2413-2419 (2001).

Geng et al., "A Specific Antagonist of the p110delta Catalytic Component of Phosphatidylinositol 3'-kinase, IC486068, Enhances Radiation-Induced Tumor Vascular Destruction", Cancer Research, vol. 64, No. 14, pp. 4893-4899 (2004).

Grimes and Jope, "CREB DNA binding activity is inhibited by glycogen synthase kinase-3 Beta and facilitated by lithium". Journal of Neurochemistry, vol. 78, No. 6, pp. 1219-1232 (2001).

Hongisto et al., "Lithium Blocks the c-Jun Stress Response and Protects Neurons via Its Action on Glycogen Synthase Kinase 3", Molecular and Cellular Biology, vol. 23, No. 17, pp. 6027-6036 (2003).

Klein and Melton, "A molecular mechanism for the effect of lithium on development", Proceedings of the National Academy of Sciences of the United States of America, vol. 93, pp. 8455-8459 (1996).

Mao et al., "Lithium Inhibits Cell Cycle Progression and Induces Stabilization of p53 in Bovine Aortic Endothelial Cells", Journal of Biological Chemistry, vol. 276, No. 28, pp. 26180-26188 (2001).

Nonaka et al., "Chronic lithium treatment robustly protects neurons in the central nervous system against excitotoxicity by inhibiting N-methyl-D-aspartate receptor-mediated calcium influx", Proceedings of the National Academy of Science of the United States of America, vol. 95, pp. 2642-2647 (1998).

Stambolic et al., "Lithium inhibits glycogen synthase kinase-3 activity and mimics wingless signalling in intact cells", Current Biology, vol. 6, No. 12 pp. 1664-16688 (1996).

Su et al., "Lithium, a Common Drug for Bipolar Disorder Treatment, Regulates Amyloid-beta Precursor Protein Processing", Biochemistry, vol. 43, No. 22, pp. 6899-6908 (2004).

Tan and Hallahan, "Growth Factor-Independent Activation of Protein Kinase B Contributes to the Inherent Resistance Vascular Endothelium to Radiation-Induced Apoptic Response", Cancer Research, vol. 63, pp. 7663-7667 (2003).

Bauer et al., "Implications of the Neuroprotective Effects of Lithium for the Treatment of Bipolar and Neurodegenerative Disorders," Pharmacopsychiatry. vol. 36 Suppl. 3 pp. S250-S254 (2003).

Bhat et al., "Glycogen synthase kinase 3: a drug target for CNS therapies," Journal of Neurochemistry. vol. 89 pp. 1313-1317 (2004).

Chuang et al., "Neuroprotective effects of lithium in cultured cells and animal models of diseases," Bipolar Disorders. vol. 4 pp. 129-136 (2002).

Cimarosti et al., "An investigation of the neuroprotective effect of lithium in organotypic slice cultures of rat hippocampus exposed to oxygen and glucose deprivation," Neuroscience Letters. vol. 315 pp. 33-36 (2001).

Culbert et al., "GSK-3 inhibition by adenoviral FRAT1 overexpression is neuroprotective and induces Tau dephosphorylation and β-catenin stabilisation without elevation of glycogen synthase activity," FEBS Letters. vol. 507 pp. 288-294 (2001).

De Sarno et al., "Regulation of Akt and glycogen synthase kinase-3β Phosphorylation by sodium valproate and lithium," Neuropharmacology. vol. 43 pp. 1158-1164 (2002).

Ferrer et al., "X-Ray-Induced Cell Death in the Developing Hippocampal Complex Involves Neurons and Requires Protein Synthesis," Journal of Neuropathology and Experimental Neurology. vol. 52, No. 4 pp. 370-378 (1993).

Hennion et al., "Evaluation of neuroprotection by lithium and valproic acid against ouabain-induced cell damage," Biopolar Disorders. vol. 4 pp. 201-206 (2002).

Hetman et al., "Role of Glycogen Synthase Kinase-3β in Neuronal Apoptosis Induced by Trophic Withdrawal," The Journal of Neuroscience. vol. 20, No. 7 pp. 2567-2574 (2000).

Inouye et al., "Lithium Delays the Radiation-induced Apoptotic Process in External Granule Cells of Mouse Cerebellum," J. Radiat. Res. vol. 36 pp. 203-208 (1995).

Jope, "Lithium and GSK-3: one inhibitor, two inhibitory actions, multiple outcomes," Trends in Pharmacological Sciences. vol. 24 pp. 441-443 (2003).

Kim et al., "Glycogen Synthase Kinase 3β is a Natural Activator of Mitogen-activated Protein Kinase/Extracellular Signal-regulated Kinase Kinase Kinase 1 (MEKK1)," The Journal of Biological Chemistry. vol. 278, No. 16 pp. 13995-14001 (2003).

Nonaka, S., and Chuang, D., "Neuroprotective effects of chronic lithium on focal cerebral ischemia in rats," NeuroReport. vol. 9, No. 9 pp. 2081-2084 (1998).

Tan et al., "Radiation-Induced Activation of PI3K/Akt Contributes to Endothelial Viability," International Journal of Radiation Oncology. vol. 54, No. 2 p. 26 (2002) [Abstract 40].

Tong et al., "Activation of glycogen synthase kinase 3 beta (GSK-3β) by platelet activating factor mediates migration and cell death in cerebellar granule neurons," European Journal of Neuroscience. vol. 13 pp. 1913-1922 (2001).

Watcharasit et al., "Direct, activating interaction between glycogen synthase kinase-3β and p53 after DNA damage," PNAS. vol. 99, No. 12 pp. 7951-7955 (2002).

Yang et al., "Effects of lithium on primary cultured cerebrocortical neurons of rat," Chin. J. Ind. Hyg. Occup. Dis. vol. 22, No. 3 pp. 188-190 (2004) [Abstract].

* cited by examiner

US 8,771,754 B2

USE OF GSK3 INHIBITORS IN COMBINATION WITH RADIATION THERAPIES

CROSS REFERENCE TO RELATED APPLICATIONS

This application is based on and claims priority to U.S. Provisional Application Ser. No. 60/611,430, filed Sep. 17, 2004, the disclosure of which is herein incorporated by reference in its entirety.

GRANT STATEMENT

This work was supported by grants, R01-CA89674, P30-CA68485, R01-CA112385, R01-CA88076, and P50-CA90949 from the National Institutes of Health, P50-CA90949 from the Vanderbilt Lung Cancer SPORE, and CCSG P30-CA68485 from the Vanderbilt-Ingram Cancer Center. Thus, the U.S. government has certain rights in the presently disclosed subject matter.

TECHNICAL FIELD

The presently disclosed subject matter relates generally to the fields of molecular biology and medicine. More particularly, it concerns the use of inhibitors of glycogen synthase kinase 3 (GSK3) in combination with radiation therapies.

BACKGROUND ART

Radiation therapies are commonly used to treat individuals with diseases such as cancer, and significant deleterious side effects can be associated with radiation therapies. These side effects can include, for example in the case of cranial radiation therapy, memory loss, neuron death, and cognitive decline. Other side effects can include damage to the visual system (Lessell, 2004), and damage to tissues of various internal organs and the vasculature. In many cases, the side effects associated with radiation therapy can be quite severe and even crippling. Thus, there exists a significant need for methods to ameliorate the deleterious side effects associated with radiation therapies.

Certain approaches have been evaluated in attempts to enhance the efficacy of radiation therapies. Phosphatidylinositol 3-kinase (PI3K) inhibitors, such as wortmannin and LY294002, have been shown to increase the sensitivity of tumor vasculature to destruction and apoptosis when given in combination with radiation therapies (Edwards et al., 2002; Tan and Hallahan, 2003; Geng et al., 2004). Inhibition of vascular endothelial growth factor receptor signaling using the sFLK-1 inhibitor SU5416 enhanced the destruction of tumor vasculature (Geng et al., 2001).

Inhibitors of glycogen synthase kinase 3 (GSK3) have been provided for use in treating ailments such as Alzheimer's and Parkinson's disease (Cohen and Goedert, 2004). Lithium is a GSK3 inhibitor that has been used as a mood-stabilizing drug for over fifty years, and lithium can protect neurons against several kinds of neurotoxic insults including trophic deprivation and excititoxicity (Hongsito et al., 2003; Nonaka et al., 1998; Klein and Melton 1996; Cimarosti et al., 2001; Hennion et al 2002; Nonaka and Chuang 1998; Jope, 2003). The potential for using a GSK3 inhibitor in combination with a radiation therapy has not been evaluated prior to the presently disclosed subject matter.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to some embodiments of the presently disclosed subject matter, whether listed in this Summary or not. To avoid excessive repetition, this Summary does not list or suggest all possible combinations of such features.

The presently disclosed subject matter provides methods involving the use of GSK3 inhibitors in combination with a radiation therapy. These methods, in some embodiments, result in an amelioration of one or more of cognitive decline, toxicity to vascular endothelial cells, and neuron death associated with radiation therapy alone.

An aspect of the presently disclosed subject matter relates to a method of treating a hyperproliferative disease. In some embodiments, the method comprises administering radiation therapy and a pharmaceutical composition comprising a small molecule GSK3 inhibitor to a subject. In some embodiments, said subject is a mammal, such as a human. In some embodiments, the GSK3 inhibitor is administered in a pharmaceutically acceptable carrier, diluent, or vehicle. In some embodiments, the GSK3 inhibitor is administered to said subject intranasally, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctivally, intravesicularlly, mucosally, intrapericardially, intraumbilically, intraocularally, orally, topically, locally, via inhalation, via injection, via infusion, via continuous infusion, via localized perfusion to a tumor, by bathing target cells directly, via a catheter, via a lavage, in a creme, in lipid compositions, or by any combination of the forgoing. In some embodiments, the tumor is a cancerous tumor. In some embodiments, the tumor can be a brain tumor or a lung tumor.

In some embodiments, the hyperproliferative disease is a benign tumor, an arterovenous malformation, a neuroma (e.g., an acoustic neuroma or an optic neuroma), a meningioma, a schwanoma, an adenoma (e.g., a pituitary adenoma), or a glioma (e.g., an optic glioma). The benign tumor can be, for example, a brain tumor, a spinal cord tumor, an eye tumor, or a lung tumor.

In some embodiments, the hyperproliferative disease is cancer. In some embodiments, the cancer can comprise lung cancer, prostate cancer, ovarian cancer, testicular cancer, brain cancer, skin cancer, colon cancer, gastric cancer, esophageal cancer, tracheal cancer, head and neck cancer, pancreatic cancer, liver cancer, breast cancer, ovarian cancer, lymphoid cancer, leukemia, cervical cancer, or vulvar cancer. In some embodiments, the cancer comprises brain cancer or lung cancer. In some embodiments, the radiation therapy comprises cranial radiation therapy.

In some embodiments, the administering comprises administering a sufficient amount of said GSK3 inhibitor to result in a reduction in toxicity to neurons. The neurons can comprise neurons of the central nervous system, such as hippocampal neurons, or neurons of the peripheral nervous system. In some embodiments, the toxicity can comprise neuron death and/or apoptosis. In some embodiments, the administering comprises administering a sufficient amount of said GSK3 inhibitor to result in a reduction in cognitive decline of said subject. In some embodiments, the administering comprises administering a sufficient amount of said GSK3 inhibitor to result in a reduction in toxicity to non-neuronal cells.

In some embodiments, the non-neuronal cells are vascular endothelial cells. The non-neuronal cells can be, for example, salivary gland cells, GI tract cells, lung cells, liver cells, or vascular endothelial cells.

In some embodiments, the toxicity comprises death of said cells. In some embodiments, the toxicity comprises apoptosis of said cells. In some embodiments, the reduction of toxicity comprises an elimination of toxicity. In some embodiments, the method further comprises administering a second pharmaceutical composition. In some embodiments, the second pharmaceutical composition comprises an anti-cancer composition.

It is provided that any GSK3 inhibitor that is currently known or which can be discovered can be used with the presently disclosed subject matter. In some embodiments, the GSK3 inhibitor is lithium. In some embodiments, the GSK3 inhibitor can also be N-(4-methoxybenzyl)-N'-(5-nitro-1,3-thiazol-2-yl)urea (AR-A014418), 4-acylamino-6-arylfuro[2,3-d]pyrimidine, SB-415286, CT98014, or CHIR98023. In some embodiments, the GSK3 inhibitor can comprise a genetic construct, such as a siNA, siRNA, antisense nucleic acid, or can encode dominant negative GSK3 polypeptide.

It is also provided that any embodiment discussed in this specification can be implemented with respect to any method or composition of the presently disclosed subject matter, and vice versa. Furthermore, compositions of the presently disclosed subject matter can be used to achieve the methods of the presently disclosed subject matter.

Accordingly, it is an object of the presently disclosed subject matter to provide a method for treating a hyperproliferative disease. This object is achieved in whole or in part by the presently disclosed subject matter.

An object of the presently disclosed subject matter having been stated above, other objects and advantages will become apparent to those of ordinary skill in the art after a study of the following lDescription of the presently disclosed subject matter, Drawings, and non-limiting Examples.

BRIEF DESCRIPTION OF THE DRAWINGS

The following drawings form part of the present specification and are included to further demonstrate some embodiments of the presently disclosed subject matter. The presently disclosed subject matter can be better understood by reference to one or more of these drawings in combination with the detailed description of specific embodiments presented herein.

In FIG. 2A, mouse HT-22 hippocampal neuronal cells, mouse GL261 glioblastoma cells, and mouse Daoy medulloblastoma cells were treated with 3 mM LiCl followed by irradiation with the indicated doses. Shown are the surviving fractions of cells treated with seven days of lithium (○) or without lithium (●) in clonogenic assays. *P=0.047. In FIG. 2B, mouse hippocampal neuronal cells HT-22 were treated with GSK3β inhibitors prior to irradiation with 3 Gy. Cells were collected 24 hours after irradiation, stained with Annexin V-FITC and propidium iodide, and analyzed by flow cytometry. FIG. 2C depicts morphologic analysis of apoptosis in irradiated HT-22 hippocampal neuronal cells performed under microscopy following DAPI staining. Apoptotic and non-apoptotic cells were counted in multiple randomly selected fields. The percentage of apoptotic cells (+/−SEM) is presented as the percentage of total cells.

FIG. 3A depicts photographs (200×) of mouse hippocampus treated with 0 Gy, 2 Gy, 4 Gy, and 10 Gy. The subgranular zone is highlighted in the 0 Gy depiction of FIG. 3A. Arrows point to examples of pyknotic cells. Eight high-powered fields (HPFs, 400×) were observed and counted for each experimental group. FIG. 3B summarizes the number of pyknotic cells per HPF for each experimental group.

FIG. 4G depicts the average number of TUNEL positive cells per HPF in each treatment group.

In FIG. 5A, HT-22 mouse hippocampal neuronal cells were treated with 3 mM LiCl for 1, 3, and 5 days. In FIGS. 5B and 5C, HT-22 cells were treated with 3 mM LiCl for 7 days, then irradiated with 3 Gy and harvested at 30 minutes (FIG. 5B) or 6 hours (FIG. 5C) after radiation. In FIG. 5D, HT-22 cells were treated with LiCl or SB415286, then irradiated with 3 Gy and harvested at 6 hours after radiation. Cells were lysed and total protein was analyzed by Western blot analysis (40 g protein/lane). Antibodies to phospho-GSK3β (Ser 9 and Tyr 216), and total GSK3β, Akt, phospho-Akt (Ser 473), β-catenin, cyclin D1, Bax, and Bcl-2 were used to analyze levels of expression of these proteins. Actin was used to evaluate protein loading in each lane.

FIG. 9A depicts Western blots probed with antibodies specific for phosphorylated Akt and total Akt. FIG. 9B depicts Western blots probed with antibodies specific for phosphorylated GSK3β and total GSK3β. FIG. 9C depicts Western blots probed with antibodies specific for phosphorylated GSK3β and total GSK3β of protein extracted 30 minutes after HUVEC were treated with the indicated doses of radiation. FIG. 9D depicts Western blots using the antibody that is specific for phosphorylated GSK3β and antibody that binds to total GSK3β of HUVEC irradiated with 3 Gy 24 hours after being transduced with Ad.GFP or Ad.ΔAkt. Protein was extracted following irradiation and separated by 8% PAGE gel.

FIG. 10A depicts propidium iodide-stained HUVEC following treatment with radiation alone, Ad.ΔAkt alone, Ad.ΔAkt followed by 3 Gy, and untreated controls. FIG. 10B presents a bar graph showing the average percentage of cells with apoptotic nuclei and SEM from three experiments. FIG. 10C depicts a Western blot using antibodies to intact caspase 3 showing caspase 3 cleavage in irradiated endothelial cells. HUVEC were treated with Ad.ΔAkt or Ad.GFP followed by irradiation by 3 Gy or 0 Gy. Total cellular protein was extracted and separated by PAGE. *P<0.05.

FIGS. 11A-11D depict capillary-tubule formation attenuation in irradiated endothelial cells by Ad.ΔAkt. HUVEC were transduced with Ad.ΔAkt or vectors and treated with 4 Gy or 0 Gy. Cells were immediately cultured onto MATRIGEL™ Basement Membrane Matrix. The formation of capillary-like structures was monitored for 24 hours. Depicted are representative photographs of capillary tubule formation 24 hours after treatment with Ad.GFP (FIG. 11A), Ad.ΔAkt alone (FIG. 11B), 4 Gy alone (FIG. 11C), or Ad.ΔAkt+4 Gy (FIG. 11D). The bar graph presented in FIG. 11E shows the mean and standard error of the mean of the three capillary formation experiments in MATRIGEL™ Basement Membrane Matrix. *P<0.01.

FIG. 12D presents a bar graph depicting the mean and standard error of the mean of the percentage of cells with apoptotic nuclei from 3 experiments. *P<0.05. FIGS. 12E-12H depict caspase 3 activity evaluated in response to radiation and/or lithium under the stated conditions.

FIG. 13A presents a bar graph depicting tumor blood vessels development within the model over the course of 1 week after tumor implantation under the stated conditions. The bar graph shows the mean and SEM of 3 mice entered into each of the treatment groups. P<0.05. FIGS. 13B-13F depict fluorescence microscopy images of capillaries after MATRIGEL™ Basement Membrane Matrix containing VEGF and adenoviral vectors, Ad.ΔAkt and Ad.DN-GSK3β were implanted subcutaneously in the flanks of mice. Flanks were then treated with radiation three times at 3 Gy each day over 72 hours. FITC-labeled dextran was injected by tail vein and MATRIGEL™ Basement Membrane Matrix plugs were excised 30 minutes later and imaged by fluorescence microscopy. Shown are fluorescence microscopy images of capillaries of an untreated control (FIG. 13B) and following treatment with Ad.ΔAkt alone (FIG. 13C), 3 Gy alone (FIG. 13D), Ad.Δ-Akt+3 Gy (FIG. 13E), and Ad.ΔAkt+Ad.DN-GSK3+3 Gy (FIG. 13F). FIG. 13G presents a bar graph depicting the percent change in capillary tubules following treatment with the indicated. *P<0.05.

DETAILED DESCRIPTION

Figure 1:
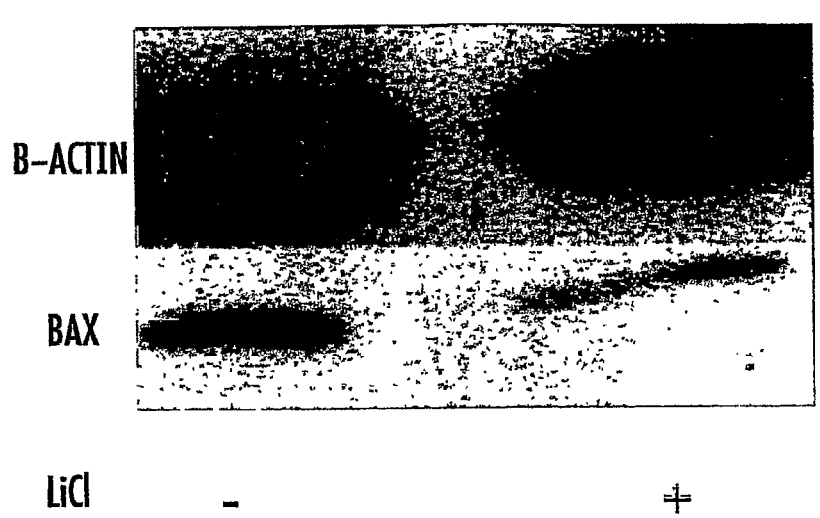
FIG. 1 depicts a Western immunoblot with antibody specific for Bax. HT-22 cells were treated with 3 mM LiCl for 7 days, and total cellular protein was extracted. β-actin is used to demonstrate equal loading of protein.

The presently disclosed subject matter addresses deficiencies in the prior art by providing methods involving the use of GSK3 inhibitors in combination with a radiation therapy. These methods, in some embodiments, result in an amelioration of cognitive decline, toxicity to vascular endothelial cells, and/or neuron death associated with radiation therapy alone.

I. Definitions

Following long-standing patent law tradition, the terms "a", "an", and "the" are meant to refer to one or more as used herein, including the claims. For example, the phrase "a cell" can refer to one or more cells. Also as used herein, the term "another" can mean at least a second or more.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "therapeutic agent" as used herein is defined as an agent that provides treatment for a disease or medical condition. The agent in some embodiments improves at least one symptom or parameter of the disease or medical condition. For instance, in tumor therapy, the therapeutic agent reduces the size of the tumor, inhibits or prevents growth or metastases of the tumor, or eliminates the tumor. Examples include a drug, such as an anticancer drug, a gene therapy composition, a radionuclide, a hormone, a nutriceutical, or a combination thereof.

The term "tumor" as used herein is defined as an uncontrolled and progressive growth of cells in a tissue. A skilled artisan is aware other synonymous terms exist, such as neoplasm or malignancy. In some embodiments, the tumor is a solid tumor. In some embodiments, the tumor derives, either primarily or as a metastatic form, from cancers such as of the liver, prostate, pancreas, head and neck, breast, brain, colon, adenoid, oral, skin, lung, testes, ovaries, cervix, endometrium, bladder, stomach, and epithelium.

The term "drug" as used herein is defined as a compound that aids in the treatment of disease or medical condition or which controls or improves any physiological or pathological condition associated with the disease or medical condition. In some embodiments, the drug is a GSK3 inhibitor.

The term "anticancer drug" and "anti-cancer compound" as used herein are defined as a drug for the treatment of cancer, such as for a solid tumor. In some embodiments, the anticancer drug reduces the size of the tumor, inhibits or prevents growth or metastases of the tumor, and/or eliminates the tumor.

The term "small molecule" refers to a molecule that is not a hormone. The small molecule is in some embodiments less than 100 kDa. Thus, insulin is not a small molecule as defined herein.

II. GSK3 Inhibitors

Some embodiments of the presently disclosed subject matter employ GSK3 inhibitors in combination with a radiation therapy. In some embodiments of the presently disclosed subject matter, the GSK inhibitor is an inhibitor that acts directly on GSK3. Glycogen synthase kinase 3 (GSK3 or GSK-3) was initially identified as an enzyme that regulates glycogen synthesis in response to insulin (Welsh et al., 1996). GSK3 is also involved in the modulation of the transcription factors AP-1 and CREB, and GSK3 is a substrate of the protein kinase Akt (Cross et al., 1995). GSK3 is a protein-serine/threonine kinase whose activity is inhibited by Akt phosphorylation in response to growth factor stimulation.

GSK3 phosphorylates a broad range of substrates including glycogen synthase, several transcription factors, and translation initiation factor eIF2B (Welsh et al., 1996). GSK3 is also involved in the phosphatidylinositol 3-kinase (PI3-kinase)/Akt cell survival pathway (Pap and Cooper, 1998). Additionally, GSK3 has been implicated in the regulation of cell fate in *Dictyostelium* (Harwood et al., 1995) and is a component of the Wnt signaling pathway required for *Drosophila* and *Xenopus* development (Sigfried et al., 1992; He et al., 1995; Pierce et al., 1995; Dominguez et al., 1995). Taken together, GSK3 is involved in multiple cellular processes including metabolism, cell survival, proliferation, and differentiation.

Several GSK3 inhibitors have been identified. GSK inhibitors include AR-A014418, 4-Acylamino-6-arylfuro[2,3-d]pyrimidines, lithium, SB-415286, P24, CT98014, and CHIR98023. Insulin has also been shown to be able to inhibit GSK3. These examples of GSK inhibitors are merely used for illustrative purposes and are not intended to be in any way limiting. It is provided that virtually any GSK3 inhibitor that is currently known, and/or any GSK3 inhibitor that can be subsequently discovered or created, can be employed with the presently disclosed subject matter.

II.A. GSK3 Inhibition Using Genetic Constructs

Additionally, in some embodiments of the presently disclosed subject matter, genetic constructs such as dominant negative constructs, small inhibitory nucleic acids (siNA), small inhibitory RNA (siRNA), and/or antisense can be used to inhibit GSK3 activity. In some embodiments, gene therapy approaches can be used to deliver the genetic constructs to a subject, resulting in inhibition of GSK3 in the subject. Gene therapy approaches are known in the art and include the use of viral vectors including adenoviruses, adeno-associated viruses, and lambda viruses.

II.A.1. DNA Delivery Using Viral Vectors

The ability of certain viruses to infect cells and/or enter cells via receptor-mediated endocytosis and/or to integrate into host cell genome and/or express viral genes stably and/or efficiently have made them attractive candidates for the transfer of foreign genes into mammalian cells. Exemplary gene therapy vectors of the presently disclosed subject matter will generally be viral vectors.

Although some viruses that can accept foreign genetic material are limited in the number of nucleotides they can accommodate and/or in the range of cells they infect, these viruses have been demonstrated to successfully effect gene expression. However, adenoviruses do not integrate their genetic material into the host genome and/or therefore do not require host replication for gene expression, making them ideally suited for rapid, efficient, heterologous gene expression. Techniques for preparing replication-defective infective viruses are well known in the art.

Of course, in using viral delivery systems, one might desire to purify the virion sufficiently to render it essentially free of undesirable contaminants, such as defective interfering viral particles and/or endotoxins and/or other pyrogens such that it will not cause any untoward reactions in the cell, animal, and/or individual receiving the vector construct. A representative method for purifying the vector involves the use of buoyant density gradients, such as cesium chloride gradient centrifugation.

II.A.2. Adenoviral Vectors

A particular method for delivery of the expression constructs involves the use of an adenovirus expression vector. Although adenovirus vectors are known to have a low capacity for integration into genomic DNA, this feature is counter-balanced by the high efficiency of gene transfer afforded by these vectors. As used herein, the phrase "adenovirus expression vector" is meant to include those constructs containing adenovirus sequences sufficient to (a) support packaging of the construct and/or (b) to ultimately express a tissue and/or cell-specific construct that has been cloned therein.

The expression vector can comprise a genetically engineered form of adenovirus. Knowledge of the genetic organization of adenovirus, a 36 kb linear, double-stranded DNA virus, allows substitution of large pieces of adenoviral DNA with foreign sequences up to 7 kb (Grunhaus and Horwitz, 1992). In contrast to most retrovirus vectors, the infection of host cells with an adenovirus vector does not result in chromosomal integration of the vector-encoded sequences because adenovirus DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range, and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut-off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNA's issued from this promoter possess a 5'-tripartite leader (TPL) sequence that makes them preferred mRNA's for translation.

In a current system, recombinant adenovirus is generated from homologous recombination between a shuttle vector and a provirus vector. Due to the possible recombination between two proviral vectors, wild type adenovirus can be generated from this process. Therefore, it is convenient to isolate a single clone of virus from an individual plaque and/or examine its genomic structure.

Generation and/or propagation of the current adenovirus vectors, which are replication deficient, depend on a unique helper cell line, designated 293, which was transformed from human embryonic kidney cells by Ad5 DNA fragments and constitutively expresses E1 proteins (E1A and/or E1B; Graham et al., 1977). Since the E3 region is dispensable from the adenovirus genome (Jones and/or Shenk, 1978), the current adenovirus vectors, with the help of 293 cells, carry foreign DNA in the E1 region, the D3 region, or in both regions (Graham and Prevec, 1991). Recently, adenoviral vectors comprising deletions in the E4 region have been described (U.S. Pat. No. 5,670,488, incorporated herein by reference).

In nature, adenovirus can package approximately 105% of the wild type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines can be derived from human cells such as human embryonic kidney cells, muscle cells, hematopoietic cells, or other human embryonic mesenchymal or epithelial cells. Alternatively, the helper cells can be derived from the cells of other mammalian species that are permissive for human adenovirus. Such cells include, e.g., Vero cells or other monkey embryonic mesenchymal or epithelial cells. As stated above, a representative helper cell line is 293.

Recently, Racher et al. (1995) disclosed improved methods for culturing 293 cells and/or propagating adenovirus. In one format, natural cell aggregates are grown by inoculating individual cells into 1 liter siliconized spinner flasks (Techne, Cambridge, United Kingdom) containing 100-200 ml of medium. Following stirring at 40 rpm, cell viability is estimated with trypan blue. In another format, FIBRA-CEL® microcarriers (Bibby Sterlin, Stone, United Kingdom; 5 g/l) is employed as follows. A cell inoculum, resuspended in 5 ml of medium, is added to the carrier (50 ml) in a 250 ml Erlenmeyer flask or left stationary, with occasional agitation, for 1 to 4 hours. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 hours.

Other than the requirement that the adenovirus vector be replication defective, or at least conditionally defective, the nature of the adenovirus vector is not believed to be crucial to the successful practice of the presently disclosed subject matter. The adenovirus can be of any of the 42 different known serotypes or subgroups A-F. Adenovirus type 5 of subgroup C is an exemplary starting material in order to obtain the conditional replication-defective adenovirus vector for use in the presently disclosed subject matter. This is because Adenovirus type 5 is a human adenovirus about which a great deal of biochemical and genetic information is known, and it has historically been used for most constructions employing adenovirus as a vector.

As stated above, the typical vector according to the presently disclosed subject matter is replication defective or will not have an adenovirus E1 region. Thus, it can be most convenient to introduce the transforming construct at the position from which the E1-coding sequences have been removed. However, the position of insertion of the construct within the adenovirus sequences is not critical to the presently disclosed subject matter. The polynucleotide encoding the gene of interest can also be inserted in lieu of the deleted E3 region in E3 replacement vectors as described by Karlsson et al. (1986) and/or in the E4 region where a helper cell line and/or helper virus complements the E4 defect.

Adenovirus growth and/or manipulation is known to those of skill in the art, and exhibits broad host range in vitro and/or in vivo. This group of viruses can be obtained in high titers, e.g., $10^9$ to $10^{11}$ plaque-forming units per ml, and are highly infective. The life cycle of adenovirus does not require integration into the host cell genome. The foreign genes delivered by adenovirus vectors are episomal and, therefore have low genotoxicity to host cells. No side effects have been reported in studies of vaccination with wild type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991a; Stratford-Perricaudet et al., 1991b; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and/or stereotactic inoculation into the brain (Le Gal La Salle et al., 1993). Recombinant adenovirus and adeno-associated virus (see below) can both infect and/or transduce non-dividing human primary cells.

II.A.2. AAV Vectors

Adeno-associated virus (AAV) is another attractive vector system for use in the cell transduction of the presently disclosed subject matter as it has a high frequency of integration and it can infect non-dividing cells, thus making it useful for delivery of genes into mammalian cells, for example, in tissue culture (Muzyczka, 1992) and in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. No. 5,139,941 and U.S. Pat. No. 4,797,368, each of which is incorporated herein by reference.

Studies demonstrating the use of AAV in gene delivery include LaFace et al., 1988; Zhou et al., 1993; Flotte et al., 1993; and Walsh et al., 1994. Recombinant AAV vectors have been used successfully for in vitro and/or in vivo transduction of marker genes (Kaplitt et al., 1994; Lebkowski et al., 1988; Samulski et al., 1989; Yoder et al., 1994; Zhou et al., 1994; Hermonat and Muzyczka, 1984; Tratschin et al., 1985; McLaughlin et al., 1988) and/or genes involved in human diseases (Flotte et al., 1992; Ohi et al., 1990; Walsh et al., 1994; Wei et al., 1994). Recently, an AAV vector has been approved for phase I human trials for the treatment of cystic fibrosis.

AAV is a dependent parvovirus in that it requires co-infection with another virus (either adenovirus or a member of the herpes virus family) to undergo a productive infection in cultured cells (Muzyczka, 1992). In the absence of co-infection with helper virus, the wild type AAV genome integrates through its ends into human chromosome 19 where it resides in a latent state as a provirus (Kotin et al., 1990; Samulski et al., 1991). Recombinant AAV virus (rAAV), however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, rAAV virus is made by co-transfecting a plasmid containing the gene of interest flanked by the two AAV terminal repeats (McLaughlin et al., 1988; Samulski et al., 1989; each incorporated herein by reference) and an expression plasmid containing the wild type AAV coding sequences without the terminal repeats, for example pIM45 (McCarty et al., 1991; incorporated herein by reference). The cells are also infected and/or transfected with adenovirus and/or plasmids carrying the adenovirus genes required for AAV helper function. rAAV virus stocks made in such fashion are contaminated with adenovirus that must be physically separated from the rAAV particles (for example, by cesium chloride density centrifugation). Alternatively, adenovirus vectors containing the AAV coding regions and/or cell lines containing the AAV coding regions and/or some or all of the adenovirus helper genes could be used (Yang et al., 1994; Clark et al., 1995). Cell lines carrying the rAAV DNA as an integrated provirus can also be used (Flotte et al., 1995).

II.A.3. Retroviral Vectors

Retroviruses have promise as gene delivery vectors due to their ability to integrate their genomes into the genome of the host, transferring a large amount of foreign genetic material, to infect a broad spectrum of species and/or cell types, and to be packaged using widely available packaging cell lines (Miller, 1992).

The retroviruses are a group of single-stranded RNA viruses characterized by an ability to convert their RNA genomes to double-stranded DNA in infected cells by the process of reverse transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env, which encode capsid proteins, a polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and/or enhancer sequences, and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and/or env genes but without the LTR and/or packaging components is constructed (Mann et al., 1983). When a recombinant plasmid containing a cDNA, together with the retroviral LTR and/or packaging sequences is introduced into this cell line (e.g., by calcium phosphate precipitation), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild type replication-competent virus in the packaging cells. This can result from recombination events in which the intact sequence from the recombinant virus inserts upstream from the gag, pol, and env sequences integrated in the host cell genome. However, new packaging cell lines are now available that should greatly decrease the likelihood of recombination (Markowitz et al., 1988; Hessdorffer et al., 1990).

Gene delivery using second-generation retroviral vectors has been reported. Kasahara et al. (1994) prepared an engineered variant of the Moloney murine leukemia virus, which normally infects only mouse cells, and modified an envelope protein so that the virus specifically bound to and infected human cells bearing the erythropoietin (EPO) receptor. This was achieved by inserting a portion of the EPO sequence into an envelope protein to create a chimeric protein with a new binding specificity.

II.A.4. Other Viral Vectors

Other viral vectors can be employed as expression constructs in the presently disclosed subject matter. Vectors derived from viruses such as vaccinia virus (Ridgeway, 1988; Baichwal and Sugden, 1986; Coupar et al., 1988), sindbis virus, cytomegalovirus, and herpes simplex virus can be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. (1991) recently introduced the chloramphenicol acetyltransferase (CAT) gene into duck hepatitis B virus genome in the place of the polymerase, surface, and pre-surface coding sequences. It was co-transfected with wild type virus into an avian hepatoma cell line. Culture media containing high titers of the recombinant virus were used to infect primary duckling hepatocytes. Stable CAT gene expression was detected for at least 24 days after transfection.

In some embodiments, the gene therapy vector is based on herpes simplex virus (HSV). A factor that makes HSV an attractive vector is the size and organization of the genome. Because HSV is large, incorporation of multiple genes and/or expression cassettes is less problematic than in other, smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate, and can be grown to high titers. Thus, delivery is less of a problem, both in terms of volumes needed to attain sufficient multiplicity of infection (MOI) and in a lessened need for repeat dosing.

II.A.5. Modified Viruses

In some embodiments of the presently disclosed subject matter, the nucleic acids to be delivered are housed within an infective virus that has been engineered to express a specific binding ligand. The virus particle can thus bind specifically to the cognate receptors of the target cell and deliver the contents to the cell. A novel approach designed to allow specific targeting of retrovirus vectors was recently developed based on the modification of. a retrovirus by chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and/or against a specific cell receptor were used. The antibodies were coupled via the biotin components by using streptavidin (Roux et al., 1989). Using antibodies against major histocompatibility complex class I and/or class II antigens, Roux et al. demonstrated the infection of a variety of human cells that bore those surface antigens with an ecotropic virus in vitro (Roux et al., 1989).

II.B. Vector Delivery and Cell Transformation

Non-viral vectors can also be used to transform a cell with a genetic construct that can inhibit GSK3 activity. Suitable methods for nucleic acid delivery for transformation of an organelle, a cell, a tissue, and/or an organism for use with the current presently disclosed subject matter can include virtually any method by which a nucleic acid (e.g., DNA) can be introduced into an organelle, a cell, a tissue, or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624; 5,981,274; 5,945,100; 5,780,448; 5,736,524; 5,702,932; 5,656,610; 5,589,466; and 5,580,859; each of which is incorporated herein by reference herein in its entirety), including by microinjection (Harlan and Weintraub, 1985; and U.S. Pat. No. 5,789,215; each of which is incorporated herein by reference herein in its entirety); by electroporation (U.S. Pat. No. 5,384,253, incorporated herein by reference in its entirety; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimeret al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT International Patent Application Publication Nos. WO 94/09699 and WO 95/06128; U.S. Pat. Nos. 5,610,042; 5,322,783; 5,563,055; 5,550,318; 5,538,877; and 5,538,880; each of which is incorporated herein by reference herein in its entirety); by agitation with silicon carbide fibers (Kaeppler et al., 1990; U.S. Pat. Nos. 5,302,523 and 5,464,765, each of which is incorporated herein by reference herein in its entirety); by Agrobacterium-mediated transformation (U.S. Pat. Nos. 5,591,616 and 5,563,055, each of which is incorporated herein by reference herein in its entirety); by PEG-mediated transformation of protoplasts (Omirulleh et al., 1993; U.S. Pat. Nos. 4,684,611 and 4,952,500, each of which is incorporated herein by reference herein in its entirety); by desiccation/inhibition-mediated DNA uptake (Potrykus et al., 1985), and by any combination of such methods. Through the application of techniques such as these, organelle(s), cell(s), tissue(s), and/or organism(s) can be stably and/or transiently transformed.

II.B. 1. Ex Vivo Transformation

Methods for transfecting vascular cells and tissues removed from an organism in an ex vivo setting are known to those of skill in the art. For example, canine endothelial cells have been genetically altered by retroviral gene transfer in vitro and transplanted into a canine (Wilson et al., 1989). In another example, Yucatan minipig endothelial cells were transfected by retrovirus in vitro and transplanted into an artery using a double-balloon catheter (Nabel et al., 1989). Thus, it is provided that cells or tissues can be removed and transfected ex vivo using the nucleic acids of the presently disclosed subject matter. In some embodiments, the transplanted cells and/or tissues can be placed into an organism. In some embodiments, a recombinant (i.e., heterologous) nucleic acid is expressed in the transplanted cells or tissues.

II.B.2. Injection

In some embodiments, a nucleic acid can be delivered to an organelle, a cell, a tissue, and/or an organism via one or more injections (i.e., a needle injection), such as, for example, subcutaneously, intradermally, intramuscularly, intravenously, intraperitoneally, etc. Methods of injection of vaccines are well known to those of ordinary skill in the art (e.g., injection of a composition comprising a saline solution). Some embodiments of the presently disclosed subject matter include the introduction of a nucleic acid by direct microinjection. Direct microinjection has been used to introduce nucleic acid constructs into *Xenopus* oocytes (Harland and Weintraub, 1985). The amount of a genetic construct that can inhibit GSK3 activity used can vary upon the nature of the antigen as well as the organelle, cell, tissue, and/or organism at issue.

II.B.3. Electroporation

In some embodiments of the presently disclosed subject matter, a nucleic acid is introduced into an organelle, a cell, a tissue, and/or an organism via electroporation. Electroporation involves the exposure of a suspension of cells and DNA to a high-voltage electric discharge. In some embodiments of this method, certain cell wall-degrading enzymes, such as pectin-degrading enzymes, are employed to render the target recipient cells more susceptible to transformation by electroporation than untreated cells would be (U.S. Pat. No. 5,384,253, incorporated herein by reference in its entirety). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one can employ either friable tissues, such as a suspension culture of cells or embryogenic callus, or alternatively or in addition can transform immature embryos or other organized tissue directly. In this technique, the cell walls of the chosen cells are partially degraded by exposing them to pectin-degrading enzymes (pectolyases) or mechanically wounding in a controlled manner. Examples of some species that have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One can also employ protoplasts for electroporation transformation of plant cells (Bates, 1994; Lazzeri, 1995). For example, the generation of transgenic soybean plants by electroporation of cotyledon-derived protoplasts is described by Dhir and Widholm in PCT International Patent Application Publication No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

II.B.4. Calcium Phosphate

In some embodiments of the presently disclosed subject matter, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

II.B.5. DEAE-Dextran

In some embodiments, a nucleic acid is delivered into a cell using DEAE-dextran followed by polyethylene glycol. In this manner, reporter plasmids were introduced into mouse myeloma and erythroleukemia cells (Gopal, 1985).

II.B.5. Sonication Loading

Some embodiments of the presently disclosed subject matter include the introduction of a nucleic acid by direct sonic loading. LTK-fibroblasts have been transfected with the thymidine kinase gene by sonication loading (Fechheimer et al., 1987).

II.B.5. Liposome-Mediated Transfection

In some embodiments of the presently disclosed subject matter, a nucleic acid can be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also provided is a nucleic acid complexed with LIPOFECTAMINE™ (Invtirogen GIBCO®, Carlsbad, Calif., United States of America) or SUPERFECT™ (Qiagen Inc., Valencia, Calif., United States of America).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa, and hepatoma cells has also been demonstrated (Wong et al., 1980).

In some embodiments of the presently disclosed subject matter, a liposome can be complexed with a hemagglutinating virus (HVJ). This has been shown to facilitate fusion with the cell membrane and promote cell entry of liposome-encapsulated DNA (Kaneda et al., 1989). In some embodiments, a liposome can be complexed or employed in conjunction with nuclear non-histone chromosomal proteins (HMG-1; Kato et al., 1991). In some embodiments, a liposome can be complexed or employed in conjunction with both HVJ and HMG-1. In some embodiments, a delivery vehicle can comprise a ligand and a liposome.

II.B.6. Receptor Mediated Transfection

In some embodiments, a nucleic acid can be delivered to a target cell via receptor-mediated delivery vehicles. These vehicles take advantage of the selective uptake of macromolecules by receptor-mediated endocytosis that can occur in a target cell. In view of the cell type-specific distribution of various receptors, employment of this delivery method can add another degree of specificity to the presently disclosed subject matter.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, European Patent Application Publication 0 273 085), which establishes the operability of the technique. Specific delivery in the context of another mammalian cell type has been described (Wu and Wu, 1993; incorporated herein by reference in its entirety). In some embodiments of the presently disclosed subject matter, a ligand can be chosen to correspond to a receptor specifically expressed on the target cell population.

In some embodiments, a nucleic acid delivery vehicle component of a cell-specific nucleic acid targeting vehicle can comprise a specific binding ligand in combination with a liposome. The nucleic acid(s) to be delivered can be housed within the liposome and the specific binding ligand can be functionally incorporated into the liposome membrane. The liposome can thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In some embodiments, the nucleic acid delivery vehicle component of a targeted delivery vehicle can be a liposome itself, which can comprise one or more lipids or glycoproteins that direct cell-specific binding. For example, lactosyl-ceramide, a galactose-terminal asialganglioside, has been incorporated into liposomes and an increase in the uptake of the insulin gene by hepatocytes was observed (Nicolau et al., 1987). It is provided that the tissue-specific transforming constructs of the presently disclosed subject matter can be specifically delivered into a target cell in a similar manner.

III. Applications

III.A. Hyperproliferative Diseases

As used herein, the terms "cell proliferative diseases" or "hyperproliferative diseases" refer to disorders resulting from abnormally increased and/or uncontrolled growth of cell(s) in a multicellular organism that results in harm (e.g., discomfort or decreased life expectancy) to the multicellular organism. Hyperproliferative diseases can occur in animals or humans. Cancer is an example of a hyperproliferative disease, and some embodiments of the presently disclosed subject matter relate to the treatment of cancer.

Hyperproliferative diseases also include diseases that are not cancer, such as a pre-cancerous disease (e.g., a pre-cancerous tumor), or a non-cancerous disease. The hyperproliferative disease can be a benign tumor, such as, for example, a benign tumor of the brain, spinal cord, eye, or lung. Additional examples of hyperproliferative diseases include, but are not limited to arterovenous malformations, neuromas (e.g., acoustic neuromas, optic neuromas), meningiomas, schwanomas, adenomas (e.g., a pituitary adenoma), and gliomas (e.g., optic gliomas).

In some embodiments, the presently disclosed subject matter is useful for the treatment of cancer. The cancer can be metastatic or non-metastatic. Many kinds of cancer have been identified and are well known in the art. Cancer includes, but is not limited to, lung cancer, prostate cancer, ovarian cancer, testicular cancer, brain cancer, skin cancer, colon cancer, gastric cancer, esophageal cancer, tracheal cancer, head and neck cancer, pancreatic cancer, liver cancer, breast cancer, ovarian cancer, lymphoid cancer, leukemia, cervical cancer, cancer of the central and/or peripheral nervous system, and vulvar cancer. In some embodiments, the cancer is brain cancer.

III.B. Radiation Therapies

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are generally able to repair themselves and function properly. Radiotherapy can be used to treat localized solid tumors, such as cancers of the skin, tongue, larynx, brain, breast, or cervix. It can also be used to treat leukemia and lymphoma (cancers of the blood-forming cells and lymphatic system, respectively). Certain radiation therapies have been used for nearly a century to treat human cancer (Hall, 2000).

Radiation therapy used according to the presently disclosed subject matter can include, but is not limited to, the use of γ-rays, X-rays, and/or the directed delivery of radioisotopes to tumor cells. Other forms of DNA damaging factors are also provided such as microwaves and ultraviolet (UV) irradiation. It is likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens (including, but not limited to 50, 60, 70, 80, 90, 100, 110, 120, 130, 140, 150, 160, 170, 180, 190, and 200 roentgens, as well as all intermediate dosage levels encompassed there between) for prolonged periods of time (3 to 4 weeks), to single doses of 2000 to 6000 roentgens (including, but not limited to 2000, 2500, 3000, 3500, 4000, 4500, 5000, 5500, and 6000 roentgens, as well as all intermediate dosage levels encompassed there between). Dosage ranges for radioisotopes vary widely, and depend on the half-life of the isotope, the strength and type of radiation emitted, and the uptake of the specific radioisotope by the neoplastic cells. For example, radiotherapy can be delivered at approximately 24-hour intervals at about 180-300 cGy/day. In some embodiments, twice daily fractionation (about 110-160 cGy/day) can also be employed as a radiation therapy (Schulz, 2001; Crellin, 1993).

Radiotherapy can comprise the use of radiolabeled antibodies to deliver doses of radiation directly to the cancer site (radioimmunotherapy). Antibodies are highly specific proteins that are made by the body in response to the presence of antigens (substances recognized as foreign by the immune system), although methods for producing antibodies in vitro are also known. Some tumor cells contain specific antigens that trigger the production of tumor-specific antibodies. Large quantities of these antibodies can be made in the laboratory and attached to radioactive substances (a process known as radiolabeling). Once injected into the body, the antibodies can bind to the cancer cells, which are destroyed by the cell-killing (cytotoxic) action of the radiation. This approach can minimize the risk of radiation damage to healthy cells.

Conformal radiotherapy (CRT) uses the same radiotherapy machine, a linear accelerator, as the normal radiotherapy treatment but metal blocks are placed in the path of the x-ray beam to alter its shape to match that of the cancer to ensure that a higher radiation dose is given to the tumor. Healthy surrounding cells and nearby structures receive a lower dose of radiation, so the possibility of side effects is reduced. A device called a multi-leaf collimator has been developed and can be used as an alternative to the metal blocks. The multi-leaf collimator consists of a number of metal sheets that are fixed to the linear accelerator. Each layer can be adjusted so that the radiotherapy beams can be shaped to the treatment area without the need for metal blocks. Precise positioning of the radiotherapy machine is important for conformal radiotherapy treatment, and a special scanning machine can be used to check the position of the subject's internal organs at the beginning of each treatment.

High-resolution intensity modulated radiotherapy also uses a multi-leaf collimator. During this treatment the layers of the multi-leaf collimator are moved while the treatment is being given. This method can achieve even more precise shaping of the treatment beams and can allow the dose of radiotherapy to be constant over the whole treatment area.

Although research studies have shown that conformal radiotherapy and intensity modulated radiotherapy can reduce the side effects of radiotherapy treatment, it is possible that shaping the treatment area so precisely could stop microscopic cancer cells just outside the treatment area from being destroyed. This means that the risk of the cancer coming back in the future (i.e., residual disease) can be higher with these specialized radiotherapy techniques.

Stereotactic radiotherapy can also be used to treat brain tumors. This technique directs the radiotherapy from many different angles so that the dose administered to the tumor is very high and the dose reaching surrounding healthy tissue is very low. Before treatment, several scans can be analyzed by computers to ensure that the radiotherapy is precisely targeted, and the subject's head can be held still in a specially made frame while receiving radiotherapy. Several doses can be given.

Stereotactic radio-surgery (gamma knife) for brain tumors does not use a knife, but very precisely targeted beams of gamma radiotherapy from hundreds of different angles. Only one session of radiotherapy, generally over the course of about four to five hours, is typically needed. For this treatment, a subject has a specially made metal frame attached to her or her head. Several scans and x-rays can then be carried out to find the precise area where the treatment is needed. During the radiotherapy, the subject lies with his or her head in a large helmet, which has hundreds of holes in it to allow the radiotherapy beams through.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia (i.e., the use of heat) is also being studied for its effectiveness in sensitizing tissue to radiation.

In some embodiments of the presently disclosed subject matter, the GSK3 inhibitor can be given before, during, and/or after a radiation therapy treatment. The GSK3 inhibitor can precede and/or follow the radiation therapy by intervals ranging from minutes to weeks. In embodiments where the radiation therapy and the GSK3 inhibitor are applied separately to a cell, one would generally ensure that a significant period of time did not expire between the time of each delivery, such that the GSK3 inhibitor would still be able to exert a protective effect on the cell. For example, in such embodiments, it is provided that one can contact the cell, tissue, or organism with two, three, four, or more modalities substantially simultaneously (i.e., within less than about a minute) with the GSK3 inhibitor. In some embodiments, a radiation therapy can be administered within about 1 minute, about 5 minutes, about 10 minutes, about 20 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, and/or about 48 hours or more prior to and/or after administering the GSK3 inhibitor. In some embodiments, a radiation therapy can be administered within from about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, to about 21 days prior to and/or after administering the GSK3 inhibitor. In some embodiments, it can be desirable to extend the time period for treatment significantly, however, where several weeks (e.g., about 1, about 2, about 3, about 4, about 5, about 6, about 7, or about 8 weeks or more) lapse between the administration of the GSK3 inhibitor and the radiation therapy.

Various combinations of administration of the GSK3 inhibitor ("A") and the radiation therapy ("B") can be employed, for example as follows: A/B/A; B/A/B; B/B/A; A/A/B; A/B/B; B/A/A; A/B/B/B; B/A/B/B; B/B/B/A; B/B/A/B; A/A/B/B; A/B/B/A; A/B/A/B; B/B/A/A; B/A/B/A; B/A/A/B; A/A/A/B; B/A/A/A; A/B/A/A; A/A/B/A.

Administration of the GSK inhibitor and the radiation therapy of the presently disclosed subject matter to a patient can follow general protocols for the administration of chemotherapeutics, taking into account the toxicity, if any, of the vector. It is understood that the treatment cycles can be repeated as necessary.

The actual dosage amount of a composition of the presently disclosed subject matter administered to a patient can be determined by physical and physiological factors including, but not limited to body weight, severity of condition, the type of disease being treated, previous or concurrent therapeutic interventions, idiopathy of the patient, and on the route of administration. The practitioner responsible for administration can, in any event, determine the concentration of active ingredient(s) in a composition and appropriate dose(s) for the individual subject.

In some embodiments, is can be desirable to use a radiation therapy to treat a hyperproliferative disease that is not cancer, such as a pre-cancerous disease (e.g., a pre-cancerous tumor), or a non-cancerous disease (e.g., a benign tumor). The hyperproliferative disease can thus be a benign tumor, such as, for example, a benign tumor of the brain, spinal cord, eye, or lung. Additional diseases which can be treated with a radiation therapy and could benefit from the presently disclosed subject matter include, but are not limited to, arterovenous malformations, neuromas (e.g., acoustic neuromas, optic neuromas), meningiomas, schwanomas, adenomas (e.g., a pituitary adenoma), and gliomas (e.g., optic gliomas).

Central nervous system (CNS) and peripheral nervous system (PNS) neurons, nerves, and/or regions can be damaged by radiation therapy. It is specifically envisioned that the presently disclosed subject matter can be used to protect one or more region of the CNS and/or PNS. For example, the spinal cord, optic nerve, brachial plexus, sacral nerves, and/or sciatic nerve can be damaged by radiation therapy. Thus, in some embodiments of the presently disclosed subject matter, one or more of the spinal cord, optic nerve, brachial plexus, sacral nerves, and/or sciatic nerve is protected partially or completely from a radiation therapy by administering a GSK3 inhibitor in combination with the radiation therapy.

Radiation therapies can also damage other non-neuronal tissues including tissues of the endothelium and/or vasculature (e.g., tissues comprising blood vessels), salivary glands, GI tract, lung, and/or liver. In some embodiments of the presently disclosed subject matter, a GSK3 inhibitor can be used to reduce or prevent damage from a radiation therapy to tissue of one or more non-neuronal tissue, such as a tissue of the endothelium or vasculature (e.g., tissues comprising blood vessels), salivary glands, GI tract, lung, or liver.

III.C. Combination Therapy

It is an aspect of this presently disclosed subject matter that a therapy comprising the use of a GSK3 inhibitor in combination with a radiation therapy can be used in combination with one or more additional agents or therapy methods, in some embodiments one or more additional cancer treatments. The GSK3 inhibitor and radiation therapy can precede or follow treatment with the one or more additional agents by intervals ranging from seconds to weeks. In embodiments where the one or more additional agents are applied separately to a cell, one would generally ensure that a significant period of time did not expire between the time of each delivery, such that the GSK3 inhibitor, radiation therapy, and the one or more additional agents would still be able to exert an advantageously combined effect on the cell.

For example, in some embodiments, it is provided that one can contact the cell, tissue, or organism with two, three, four or more modalities substantially simultaneously (i.e., within less than about a minute) with the GSK3 inhibitor and/or the radiation therapy. In various embodiments, one or more agents can be administered within about 1 minute, about 5 minutes, about 10 minutes, about 20 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, and/or about 48 hours or more prior to and/or after administering the GSK3 inhibitor and/or radiation therapy. In some embodiments, an agent can be administered within from about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, to about 21 days prior to and/or after administering the GSK3 inhibitor and/or the radiation therapy. In some embodiments, it can be desirable to extend the time period for treatment significantly, however, where several weeks (e.g., about 1, about 2, about 3, about 4, about 5, about 6, about 7, or about 8 weeks or more) lapse between the respective administrations.

Various combinations of the GSK3 inhibitor or radiation therapy ("A") and the secondary agent ("B"), which can be any other therapeutic agent, can be employed, for example in a treatment regimen as follows: A/B/A; B/A/B; B/B/A; A/A/B; A/B/B; B/A/A; A/B/B/B; B/A/B/B; B/B/B/A; B/B/A/B; A/A/B/B; A/B/A/B; A/B/B/A; B/B/A/A; B/A/B/A; B/A/A/B; A/A/A/B; B/A/A/A; A/B/A/A; A/A/B/A.

Administration of the therapeutic expression constructs of the presently disclosed subject matter to a subject can follow general protocols for the administration of chemotherapeutics, taking into account the toxicity, if any, of the vector. It is expected that the treatment cycles can be repeated as necessary. It also is provided that various standard therapies, as well as surgical intervention, can be applied in combination with the GSK3 inhibitor and radiation therapy. These therapies include, but are not limited to chemotherapy, immunotherapy, gene therapy, and surgery.

III.D. Chemotherapy

Cancer therapies can also include a variety of combination therapies with both chemical and radiation-based treatments. Combination chemotherapy include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, cisplatinum, 5-fluorouracil, vincristin, vinblastin, methotrexate, and/or combinations of any of the above and/or any analog or derivative variant of the above.

III.E. Immunotherapy

Immunotherapy, generally, relies on the use of immune effector cells and molecules to target and destroy cancer cells. The molecules can be, for example, an antibody specific for some marker on the surface of a tumor cell. The antibody alone can serve as an effector of therapy or it can recruit cells of the immune system to actually effect cell killing. The antibody also can be conjugated to a drug or toxin (chemotherapeutic, radionucleotide, ricin A chain, cholera toxin, pertussis toxin, etc.), and/or can serve merely as a targeting agent. Alternatively, the immune effector cell can be a lymphocyte carrying a surface molecule that interacts, either directly or indirectly, with a tumor cell target. Various effector cells include cytotoxic T cells and NK cells.

Immunotherapy could thus be used as part of a combined therapy, possibly in conjunction with gene therapy. The general approach for combined therapy is discussed below. Generally, the tumor cell bears some marker that is amenable to targeting; i.e., a marker that is not present on the majority of other cells. Many tumor markers exist and any of these can be suitable for targeting in the context of the presently disclosed subject matter. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erbB, and p155.

III.F. Gene Therapy

In some embodiments, the secondary treatment is a secondary gene therapy in which a therapeutic polynucleotide is administered before, after, or at the same time as a first therapeutic agent. Delivery of the therapeutic agent in conjunction with a vector encoding a gene product can have a combined anti-hyperproliferative effect on target tissues.

III.G. Surgery

Approximately 60% of persons with cancer will undergo surgery of some type, which includes preventative, diagnostic or staging, curative and palliative surgery. Curative surgery is a cancer treatment that can be used in conjunction with other therapies, such as the treatment of the presently disclosed subject matter, chemotherapy, radiotherapy, hormonal therapy, gene therapy, immunotherapy, and/or alternative therapies. Curative surgery includes resection in which all or part of cancerous tissue is physically or partially removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further provided that the presently disclosed subject matter can be used in conjunction with removal of superficial cancers, precancers, or incidental amounts of normal tissue.

IV. Pharmaceutical Preparations

Pharmaceutical compositions of the presently disclosed subject matter comprise an effective amount of a GSK3 inhibitor of the presently disclosed subject matter dissolved or dispersed in a pharmaceutically acceptable carrier. The phrases "pharmaceutical acceptable" and "pharmacologically acceptable" refer to molecular entities and compositions that do not produce an adverse, allergic, or other untoward reaction when administered to an animal, such as, for example, a human, as appropriate. The preparation of a pharmaceutical composition that contains at least one GSK3 inhibitor or additional active ingredient will be known to those of skill in the art in light of the present disclosure, as exemplified by *Remington's Pharmaceutical Sciences*, 18th Ed. Mack Printing Company, 1990, incorporated herein by reference. Moreover, for animal (e.g., human) administration, it will be understood that preparations should meet sterility, pyrogenicity, general safety, and purity standards as required by the United States Food and Drug Administration Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, *Remington's Pharmaceutical Sciences*, 18th Ed. Mack Printing Company, 1990, pp. 1289-1329, incorporated herein by reference) for inclusion in a pharmaceutical composition for administration to a subject. Except insofar as any conventional carrier is incompatible with the active ingredient, its use in the therapeutic or pharmaceutical compositions is provided.

The GSK3 inhibitor of the presently disclosed subject matter can comprise different types of carriers depending on whether it is to be administered in solid, liquid, or aerosol form, and whether it needs to be sterile for such routes of administration such as injection. The presently disclosed subject matter can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly (e.g., direct perfusion of a tumor), via a catheter, via a lavage, in lipid compositions (e.g., liposomes), or by other method or any combination of the forgoing as would be known to one of ordinary skill in the art (see, for example, *Remington's Pharmaceutical Sciences,* 18th Ed. Mack Printing Company, 1990, incorporated herein by reference).

In some embodiments, pharmaceutical compositions can comprise, for example, at least about 0.001-0.1% of a GSK3 inhibitor. In some embodiments, the active compound can comprise between about 2% to about 75% of the weight of the unit, or between about 25% to about 60%, for example, and any range derivable therein. In various embodiments, a dose can also comprise from about 0.1 mg/kg/body weight, about 0.5 mg/kg/body weight, about 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above.

In any case, the composition can comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal, and combinations thereof.

The GSK3 inhibitor can be formulated into a composition in a free base, neutral, or salt form. Pharmaceutically acceptable salts include the salts formed with the free carboxyl groups derived from inorganic bases such as for example, sodium, potassium, ammonium, calcium, or ferric hydroxides; or such organic bases as isopropylamine, trimethylamine, histidine, or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes), and combinations thereof. The proper fluidity can be maintained, for example, by the use of a coating, such as lecithin; by the maintenance of the required particle size by dispersion in carriers such as, for example, liquid polyol or lipids; by the use of surfactants such as, for example, hydroxypropylcellulose; or combinations thereof such methods. In some embodiments, isotonic agents, such as, for example, sugars, sodium chloride, or combinations thereof, can be included.

Sterile injectable solutions are prepared by incorporating the GSK3 inhibitor in the required amount of the appropriate solvent with various amounts of the other ingredients enumerated above, as required, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions, or emulsions, preparation methods include, but are not limited to vacuum-drying and freeze-drying techniques that yield a powder of the active ingredient plus any additional desired ingredient from a previously sterile-filtered liquid medium thereof. The liquid medium can be suitably buffered if necessary and the liquid diluent first rendered isotonic prior to injection with sufficient saline or glucose. The preparation of highly concentrated compositions for direct injection is also provided, where the use of DMSO as solvent is envisioned to result in extremely rapid penetration, delivering high concentrations of the active agents to a small area.

The composition can be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In some embodiments, prolonged absorption of an injectable composition can be brought about by the use in the compositions of agents delaying absorption, such as, for example, aluminum monostearate, gelatin, or combinations thereof.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Introduction To Examples 1-7

GSK3 Inhibitors Can Exert Radioprotective Effects on the Brain

Cranial radiation therapy is currently used for the treatment of both primary and metastatic brain tumors, as well as CNS involvement of leukemia and lymphoma. However, this treatment carries with it long term cognitive defects, especially in young children (Meadows et al., 1981; Robison et al., 1984; Silverman et al., 1984; Jannoun and Bloom, 1990), which is associated with increased unemployment in adulthood (Pui et al., 2003).

While the pathogenesis of this phenomenon is unclear, evidence suggests that it might involve radiation-induced damage to proliferating neuronal progenitor cells in the subgranular zone (SGZ) of the hippocampus (Mizumatsu et al., 2003; Ferrer et al., 1993; Peissner et al., 1999; Nagai et al., 2000). Relatively small doses of radiation have been shown to cause significant apoptosis in the subgranular zone (SGZ) of young rats and mice, as demonstrated by cellular morphology, TUNEL staining, and DNA laddering. Conversely, little to no apoptosis is observed in other areas of the cerebrum (Nagai et al., 2000). Radiation also causes a sharp and prolonged decline in neurogenesis in the SGZ (Mizumatsu et al., 2003; Peissner et al., 1999; Monje et al., 2002; Madsen et al., 2003; Tada et al., 2000. Experience from the clinic also suggests that radiation-induced damage to the hippocampus plays a significant role in patients' cognitive declines. Many of the defects seen in patients after cranial radiation are hippocampal dependent (learning, memory, and spatial processing; Abayomi, 1996; Roman and Sperduto, 1995). Furthermore, radiation to the temporal lobe, where the hippocampus is located, is associated with more pronounced cognitive deficits (Abayomi, 2002).

To this point, no pharmacologic intervention has been developed to attenuate this radiation-induced neurotoxicity. Several investigators have shown that lithium is neuroprotective against a wide variety of insults (Hongisto et al., 2003; Cimarosti et al., 2001; Nonaka and Chuang, 1998; Nonaka et al., 1998). The discovery that lithium is an inhibitor of glycogen synthase kinase 3-beta (GSK3β; Klein and Melton, 1996) might in part explain why lithium has such a neuroprotective effect. It has been proposed that lithium has a dual inhibitory effect on GSK3β, acting both as a competitive inhibitor of magnesium and an indirect inhibitor of an activating phosphatase (Jope, 2003).

GSK3β has been shown to inhibit a number of critical transcription factors involved in promoting cell survival and proliferation, including HSF-1, AP-1, Myc, NF-εB, NFAT, and CREB (Grimes and Jope, 2001). Lithium has also been shown to decrease levels of the pro-apoptotic proteins p53 and Bax while increasing levels of pro-survival Bcl-2 (Chen and Chuang, 1999).

Disclosed herein are studies of lithium chloride as a potential neuroprotective agent against radiation-induced apoptosis, analysis of the in vitro effects of lithium pretreatment on irradiated hippocampal neuron cells, as well as histologic, radiologic, and behavioral analyses of the effects of lithium treatment on irradiated animals.

Materials And Methods Used In Examples 1-7

Animals. All animal studies were conducted with the approval of the Institutional Animal Care and Use Committees (IACUC) and kept in a temperature and light-controlled environment with a 12/12 hour light/dark cycle. Timed pregnant Sprague-Dawley rats were obtained from Charles River Laboratories (Wilmington, Mass., United States of America). Timed pregnant C57BL/6J mice were obtained from the Jackson Laboratory (Bar Harbor, Me., United States of America). LiCl was dissolved in PBS (0.25-1 M) and administered via intraperitoneal injection.

Histology. To determine the numbers of apoptotic cells in the hippocampus, animals were sacrificed 10 hours after exposure to cranial radiation. The brain was removed and placed in 4% paraformaldehyde solution for two days. The tissue was subsequently dehydrated. The frontal lobes were removed before embedding in paraffin. Once the anterior hippocampus was visualized, 5 μM coronal sections were taken and placed on Superfrost Gold Plus slides (Fisher Scientific, Pittsburgh, Pa., United States of America). The sections were stained with hematoxylin and eosin in the standard fashion. TUNEL staining was performed with the DEAD-END™ Colorimetric TUNEL Assay (Promega Corp., Madison, Wis., United States of America), following the manufacturer's instructions. For the radiation dose curve generated in mice, one animal per dose was used. For the TUNEL experiments in rats, at least three animals were used were experimental group. Quantification of hippocampal apoptosis was performed as follows. The superior curvature of the hippocampus was used for quantification in all cases. The subgranular zone was identified as a 2-3 cell wide layer adjacent to the granule cell layer, facing the hilus. TUNEL positive or pyknotic cells were counted under a light microscope (400×). At least four fields were counted per animal.

Cell culture and treatment. Mouse hippocampal neuronal HT-22 cells were obtained from David Schubert (The Salk Institute; La Jolla, Calif., United States of America) and maintained in DMEM with 10% FBS and 1% penicillin/streptomycin (Invitrogen GIBCO™, Carlsbad, Calif., United States of America). Passaging was performed using pancreatin (Sigma, St. Louis, Mo., United States of America). Daoy medulloblastoma cells were obtained from the American Type Culture Collection (ATCC®; Manassas, Va., United States of America) and maintained in MEM with Earle's salts and 2 mM L-glutamine, supplemented with 0.1 mM nonessential amino acids, 1 mM sodium pyruvate, 10% FBS, and 1% penicillin/streptomycin (Life Technologies). Passaging was performed using 0.05% trypsin (Invitrogen GIBCO™). All cells were kept in a 5% $CO_2$ incubator at 37° C. Lithium chloride (LiCl, Sigma) was stored at room temperature. A stock solution was created by dissolving LiCl into the appropriate growth medium at a concentration of 100 mM. HT-22 cells were treated with 3 mM LiCl for 7 days, GSK3β inhibitor VIII (CALBIOCHEM®, a division of EMD Biosciences, Inc., San Diego, Calif., United States of America) at 1 μM in DMSO or SB415286 (Coghlan et al., 2000; available from Tocris Bioscience of Ellisville, Mo., United States of America) at 25 μM in ethanol for 24 hours prior to irradiation.

Radiation. For the radiation of cells, a Mark 1 Irradiator (J. L. Shepherd and Associates, San Fernando, Calif., United States of America) delivering 1.84 Gy/minute from a Cs-137 source was used. A turntable assured that the radiation was equally distributed. Sprague Dawley rats were anesthetized with ketamine and xylazine and exposed to cranial irradiation using a Therapax DXT 300 X-ray machine (Pantak Inc., Branford, Conn., United States of America) delivering 2.04 Gy/min at 80 kVP. Mice were anesthetized in a similar fashion or restrained in plastic tubing.

Immunoblotting. HT-22 cells were treated with radiation and/or LiCl and washed twice with PBS before being harvested using the M-PER® Mammalian Protein Extraction Reagent (Pierce Biotechnology Inc., Rockford, Ill., United States of America). Protein concentration was quantified by the Bio-Rad method. Equal amounts of protein were loaded into each well and separated by 10% SDS-PAGE gel, followed by transfer onto 0.45 μM nitrocellulose membranes. Membranes were blocked by use of 5% nonfat dry milk in PBS for 1 h at room temperature. The blots were then incubated with the antibodies overnight at 4° C. Goat antirabbit IgG secondary antibody (1:1000) was incubated for 1 h at room temperature. Immunoblots were developed by using the WESTERN LIGHTNIN™ Chemiluminescence Plus detection system (PerkinElmer Life Sciences, Boston, Mass., United States of America) according to the manufacturer's protocol and autoradiographed.

Clonogenic survival assays. After long-term treatment with lithium, cells were detached, counted by hemocytometer, and subcultured into new plates. Four culture plates were treated at each radiation dose level. After the cells had resettled (about 5 hours later), the cells were exposed to a dose of radiation. The lithium was allowed to remain on the cells overnight and was removed the following morning. After 8-10 days, the cells were fixed with 70% ethanol and stained with 1% methylene blue. Colonies with >50 cells were counted, and the surviving fraction was determined.

Apoptosis assays. HT-22 cells were treated with LiCl (3 mM) for 7 days, with GSK3β inhibitor VIII (1 μM) or SB415286 (25 μM) for 24 hours prior to irradiation. Camptothecin (5 μM) was added to the HT-22 cells 6 hours prior to harvest as a positive control for apoptosis. The HT-22 cells with or without the inhibitors were irradiated with 3 Gy and harvested 24 hours post irradiation. Annexin V-FITC (5 ng) and propidium iodide (50 ng) were added to 105 cells. Stained cells were analyzed by flow cytometry. The fraction of cells in each of the four gating windows (Q1-4) was calculated.

In separate experiments, morphologic assessment of apoptosis was performed on HT-22 cells by use of fluorescence microscopy following DAPI staining. HT-22 cells were treated with 3 mM LiCl for 7 days, irradiated with 3 Gy and collected after 8, 16 and 24 hours. Apoptotic cells were identified by the presence of nuclear condensation and fragmentation. Apoptotic and non-apoptotic cells were counted in multiple randomly selected microscopic fields. The average percentage of apoptotic cells (+/−SEM) was calculated and significance was measured by students T test.

Morris Water Maze Studies. The apparatus used was a circular pool 92 cm in diameter filled to a depth of 25 cm with water (20° C.). Mice could escape the water by finding a clear square platform, approximately 10×10 cm, hidden several millimeters beneath the water. The pool was located in a room with no windows. Many visual cues were present in the room, including two doors, a sink, and a curtain. For the initial visible platform experiments, the platform was marked with a plainly visible black flag. For the hidden platform experiments, the flag was removed and the water was made cloudy with white paint. A video camera suspended above the pool captured the subject's movements (2 frames/sec). The camera was connected to a Macintosh computer running software custom designed for analysis of Morris Water Maze studies. For the visible platform experiments, the location of the platform as well as the start location of the mouse changed for each trial. There were four possible platform locations, one in each quadrant of the pool. For the hidden platform experiment, the platform location remained constant for all trials, but the start locations changed with each trial, and the sequence of start locations varied from day to day. A trial started by placing a mouse into the water facing the wall of the pool in one of four possible start locations marked north, south, east, and west. Once placed in the water, the camera was immediately activated. Each mouse was given up to 60 seconds to locate the platform. The trial was stopped when 60 seconds had expired or the mouse remained on the platform for greater than 1 second. When a trial ended, the mouse was removed from the pool and returned to its cage. Four trials per day per mouse were performed. Trials were performed in a massed fashion; in other words, all mice underwent the first trial of the day before undergoing a second trial. The visible platform trials were conducted for five days. The animals were given two days off before beginning the hidden platform experiments, which were conducted for a total of nine days (five days, one day off, four days).

Example 1

Chronic Lithium Decreases Bax Levels In Vitro

Bax is a pro-apoptotic signaling molecule that dimerizes with bcl-2 (Oltvai et al., 1993) and directly regulates release of cytochrome c from the mitochondria (Jurgensmeier et al., 1998). In addition, Bax has been shown to be necessary for radiation-induced apoptosis in the hippocampus (Chong et al., 2000). To see if lithium treatment decreases expression of Bax in vitro, protein was extracted from treated and untreated HT-22 cells. Western immunoblotting with antibody specific for Bax is shown in FIG. 1. 7 days of 3 mM LiCl treatment significantly reduced expression of Bax in HT-22. However, it was also determined that radiation did not induce expression of Bax in HT-22 at 6, 12, or 24 hours.

Example 2

Figure 2A:
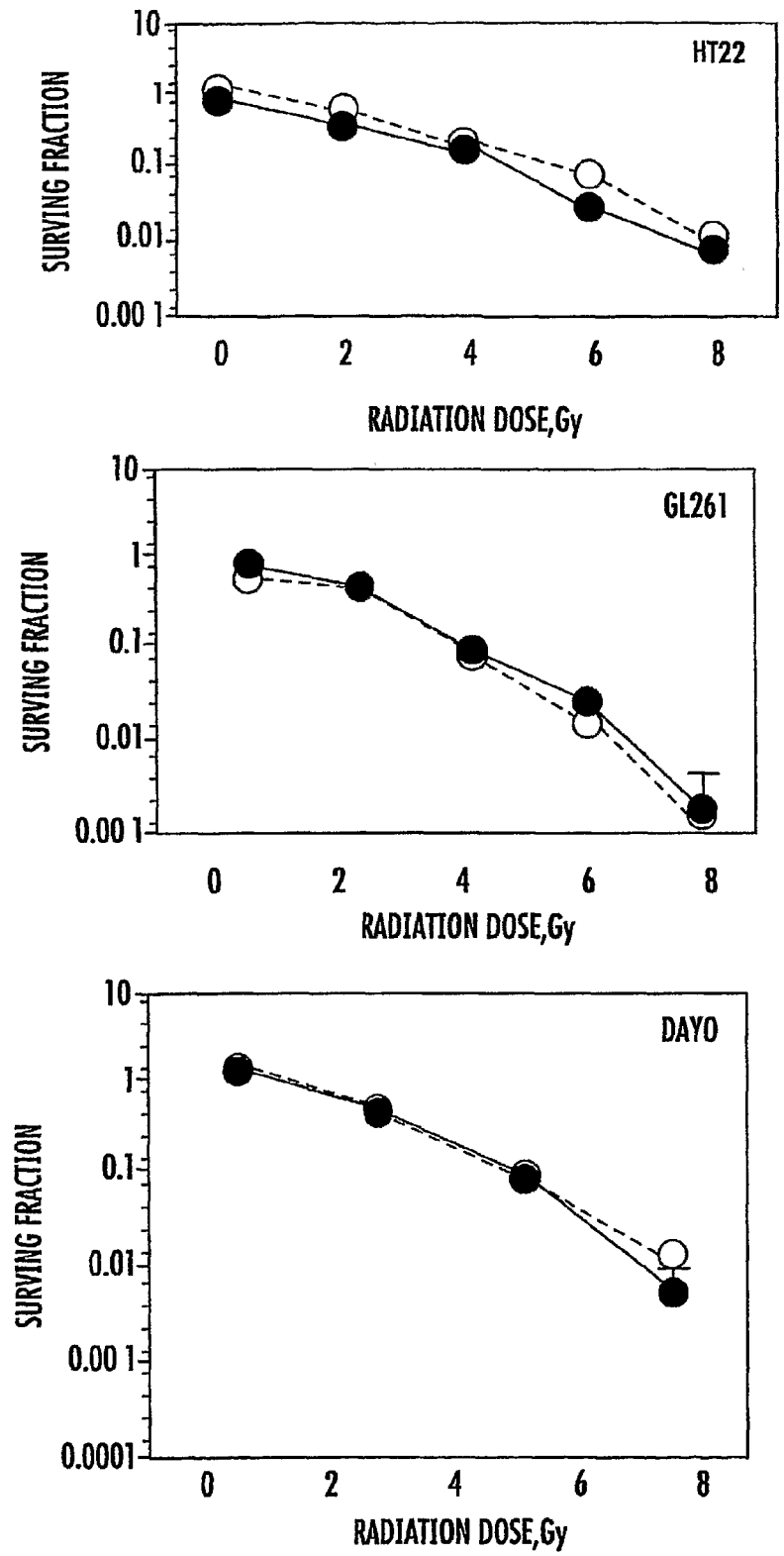
FIGS. 2A-2C depict increased survival and protection from apoptosis in irradiated HT-22 hippocampal neuronal cells induced by GSK3β inhibition.

Chronic Lithium Treatment Increases Survival of Irradiated Hippocampal Neurons, But Not Medulloblastoma Cells, In Vitro To determine whether lithium pretreatment introduces a survival benefit in irradiated hippocampal neurons compared to medulloblastoma or glioblastoma cells, HT-22, Daoy, and GL261 cells were treated with 3 mM LiCl for seven days. Cells were irradiated and survival was determined by clonogenic and apoptosis analysis. LiCl treatment demonstrated a selective increased survival of irradiated hippocampal neurons, while it had no effect on the survival of irradiated Daoy or GL261 cells (see FIG. 2A).

Example 3

Figure 2B:
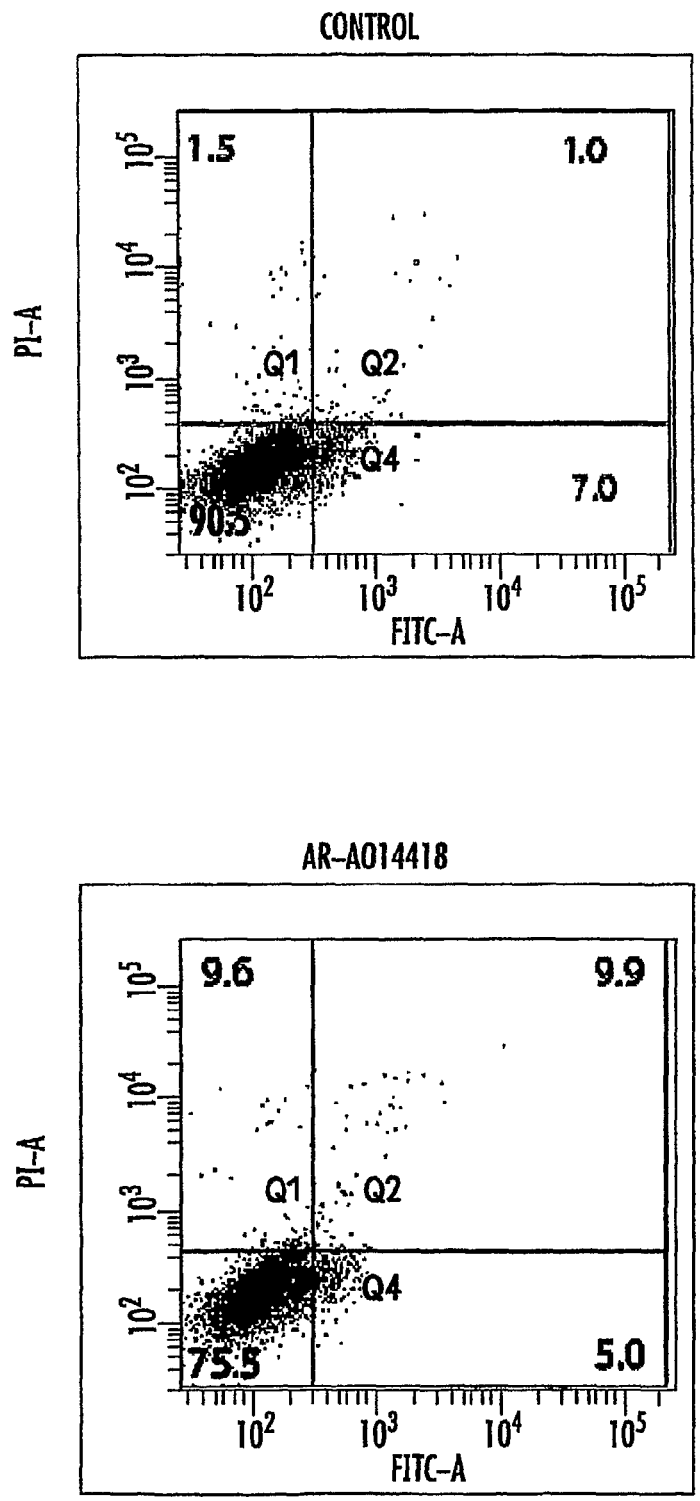
Figure 2B:
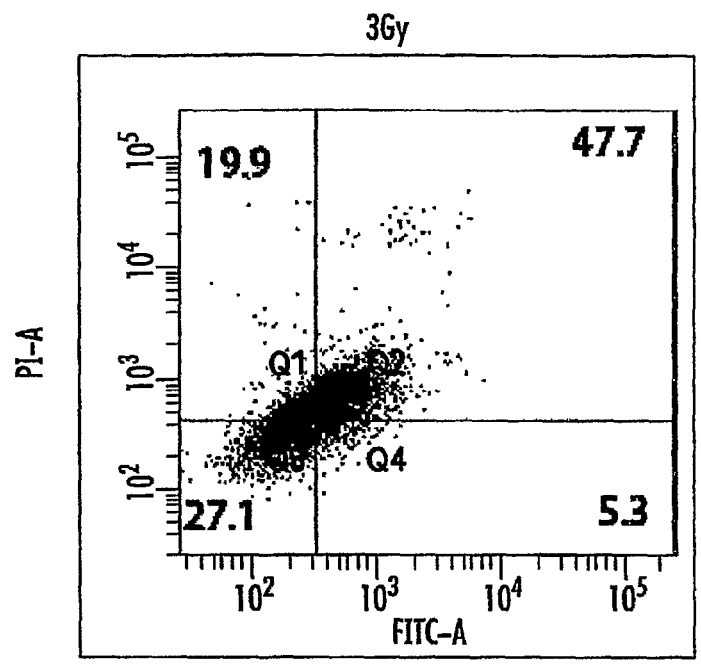
Figure 2B:
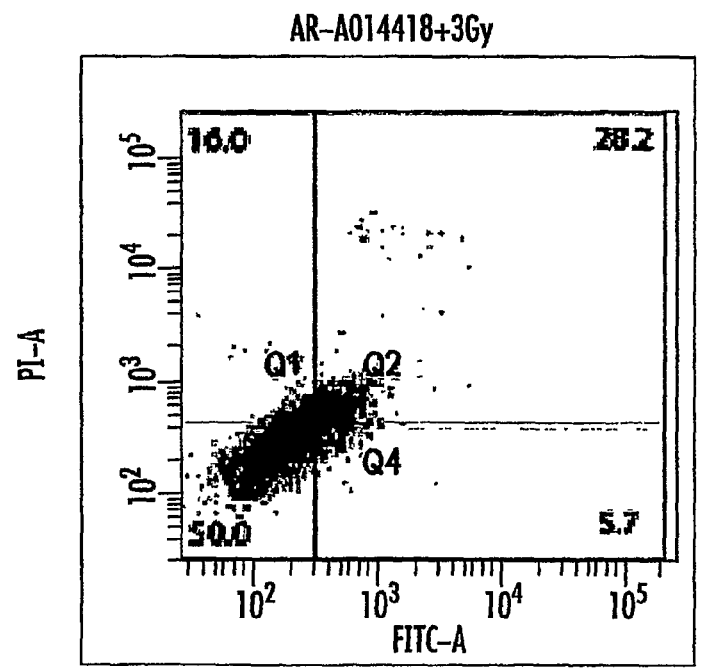
Figure 2B:
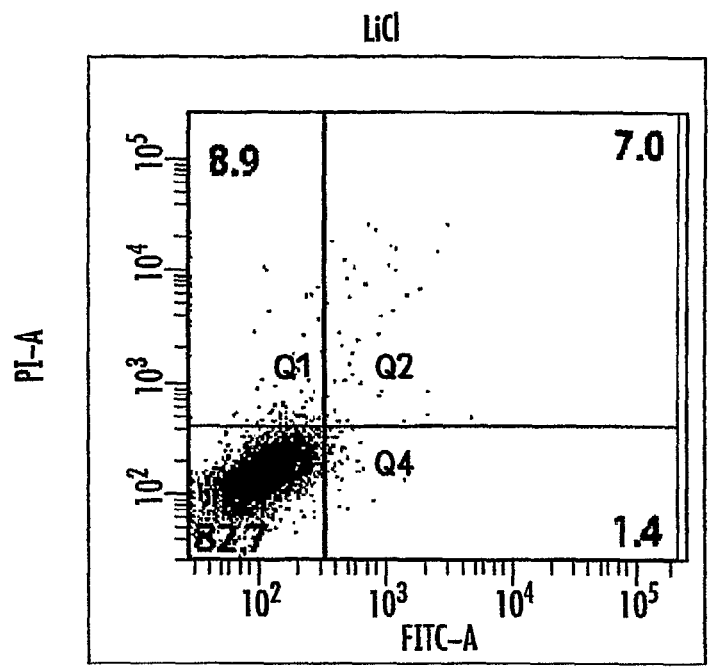
Figure 2B:
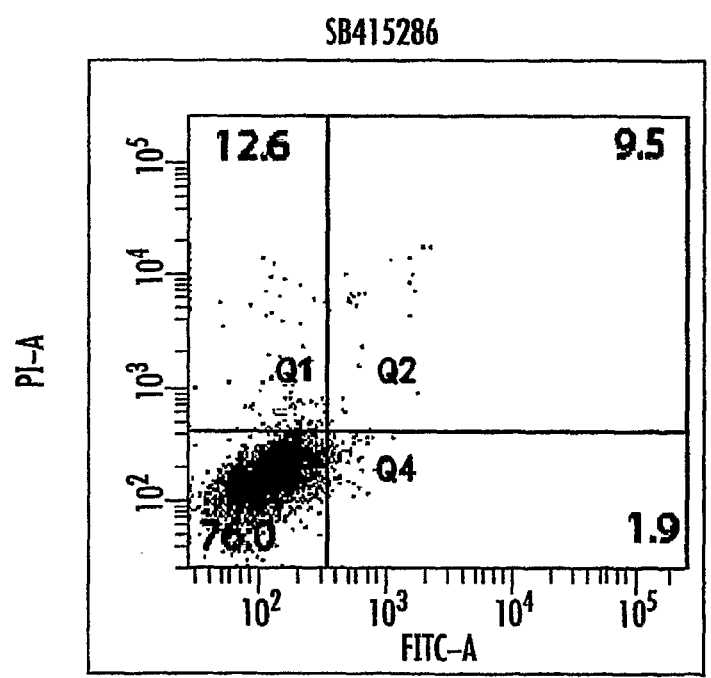
Figure 2B:
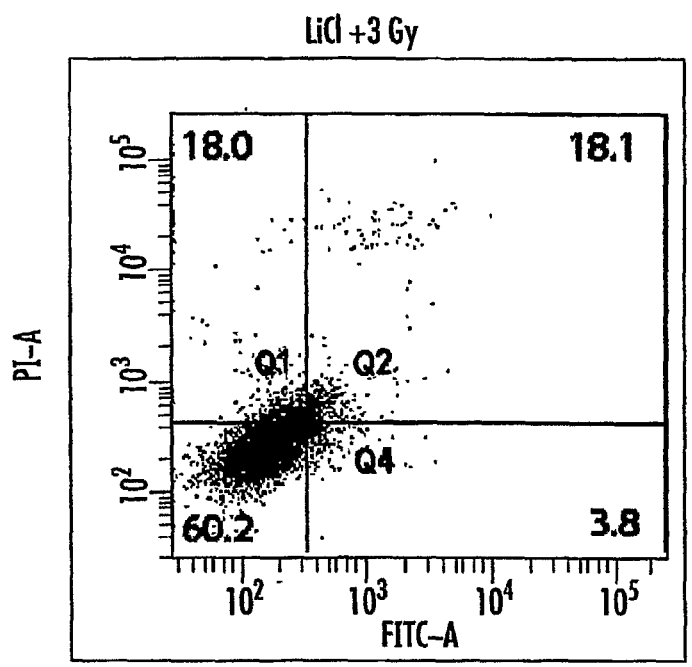
Figure 2B:
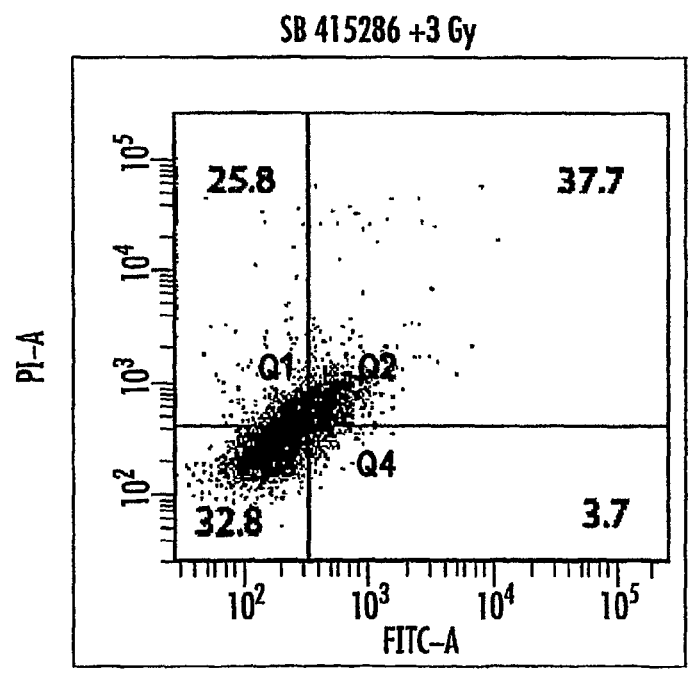
Figure 2B:
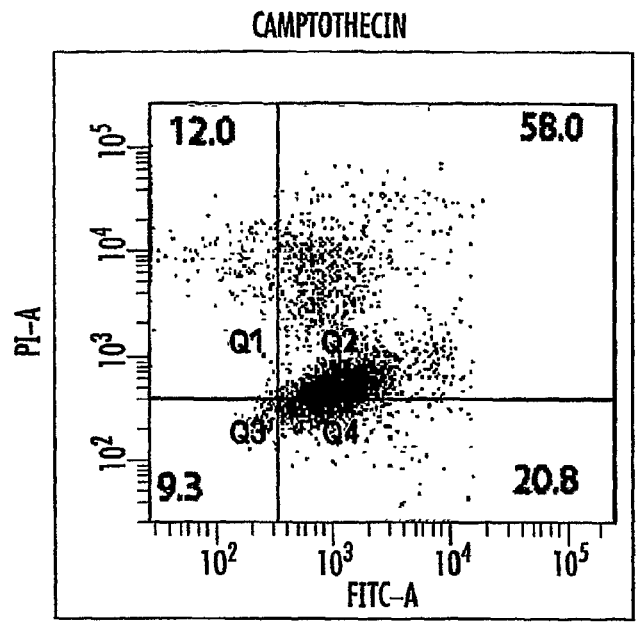
Figure 2C:
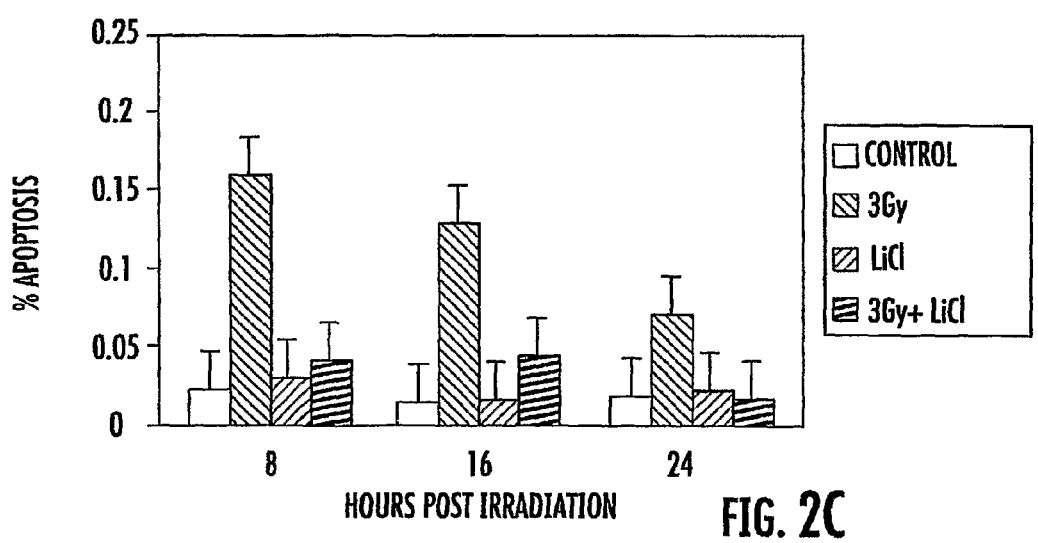

LiCl and GSK3 Inhibitors Attenuate Radiation-induced Apoptosis in Hippocampal Neurons Apoptosis was studied in irradiated mouse HT-22 hippocampal neuronal cells pretreated with LiCl, GSK3β inhibitor VIII or SB415286. Flow cytometry results following annexin V-FITC and propidium iodide staining of HT-22 cells are shown in FIG. 2B. The fraction of cells in each of the four gating windows (Q1-4) was calculated and tabulated as the mean and SEM of 3 separate experiments. Camptothecin served as positive control for apoptosis and was added to HT-22 cells prior to staining for apoptosis. Camptothecin positive control induced apoptosis in 78.8% of cells. In comparison, 3 Gy irradiation induced apoptosis in 53% of cells, while 8% of untreated control cells stained positive for apoptosis (FIG. 2B). GSK3β inhibitor VIII and SB415286 attenuated radiation-induced apoptosis in hippocampal neuronal cells to 33.9% and 41.4%, respectively (P<0.05, 3 Gy vs. 3 Gy+GSK3β inhibition). Lithium, as a nonspecific neuroprotector, attenuated radiation-induced apoptosis to 21.9% of cells (P=0.01, 3 Gy vs. 3 Gy+LiCl). The radioprotective effect of lithium in HT-22 neuronal cells was also analyzed by morphologic analysis using DAPI staining. This showed up to a 4-fold increase in survival of LiCl-treated cells as compared to cells treated with radiation alone (see FIG. 2C).

Example 4

Radiation-induced Apoptosis in the SGZ is Dose Dependent

Figure 3:
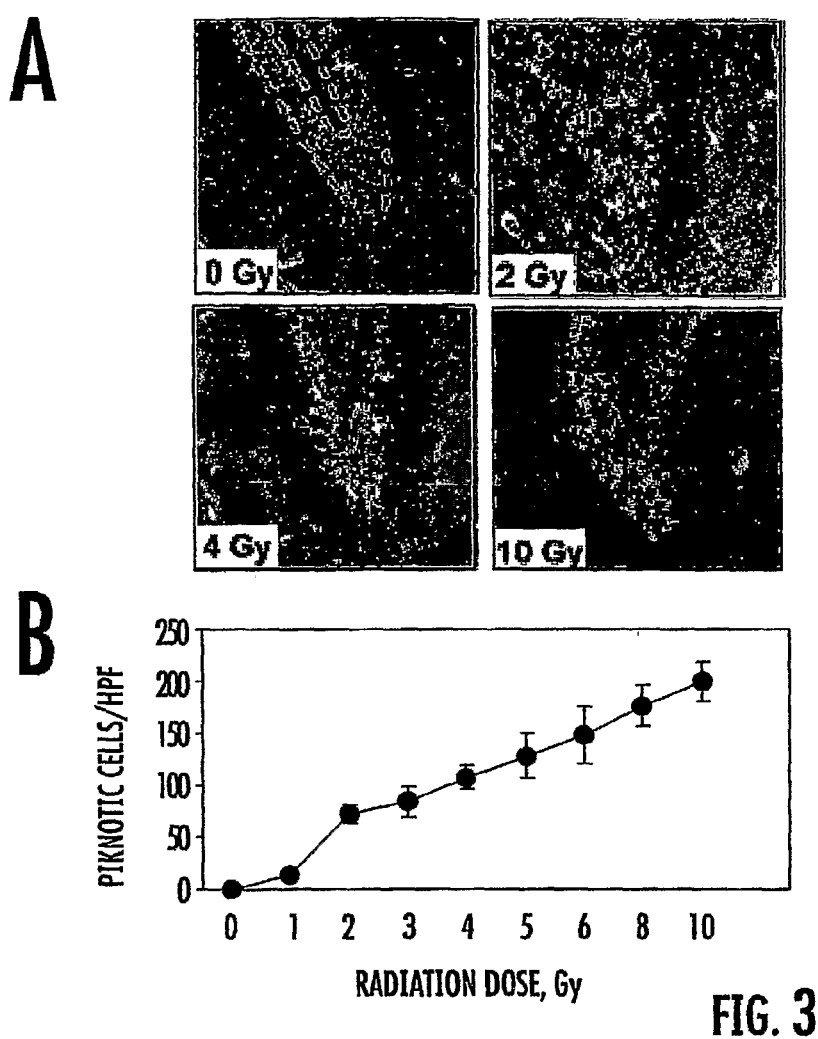
FIGS. 3A and 3B depict the results of treating two-week-old C57BL/6 mice with the indicated dose of cranial radiation. 10 hours after treatment, the animals were sacrificed. Their brains were immediately removed, fixed, embedded, and sectioned coronally. Sections that contained hippocampus were stained with Hematoxylin and Eosin (H&E).

To determine the effect of radiation dose on the amount of apoptosis in the SGZ, two-week-old mice were exposed to various doses of cranial radiation, and sacrificed 10 hours later. Coronal sections of hippocampus were prepared and stained with H&E. Pyknotic nuclei were counted within the SGZ of control in irradiated mouse brains. As shown in FIG. 3A, a dose as low as 1 Gy induced apoptosis in the neuronal precursor cells of the SGZ as compared to no TUNEL staining in untreated controls. Two Gy produced a significant increase in pyknotic nuclei to 70 per HPF (p=0.001). A dose-dependent increase in SGZ neuronal apoptosis was observed (see FIG. 3B).

Example 5

Chronic Lithium Treatment Attenuates Radiation-induced Apoptosis in the SGZ of Infant Rats To determine if lithium could attenuate radiation induced apoptosis in the SGZ, one-week old infant rats were treated with daily IP injections of LiCl beginning on postnatal day 7. On postnatal day 14, the animals were cranially irradiated. Ten hours later, sections of hippocampus were stained for apoptosis using TUNEL.

Figure 4:
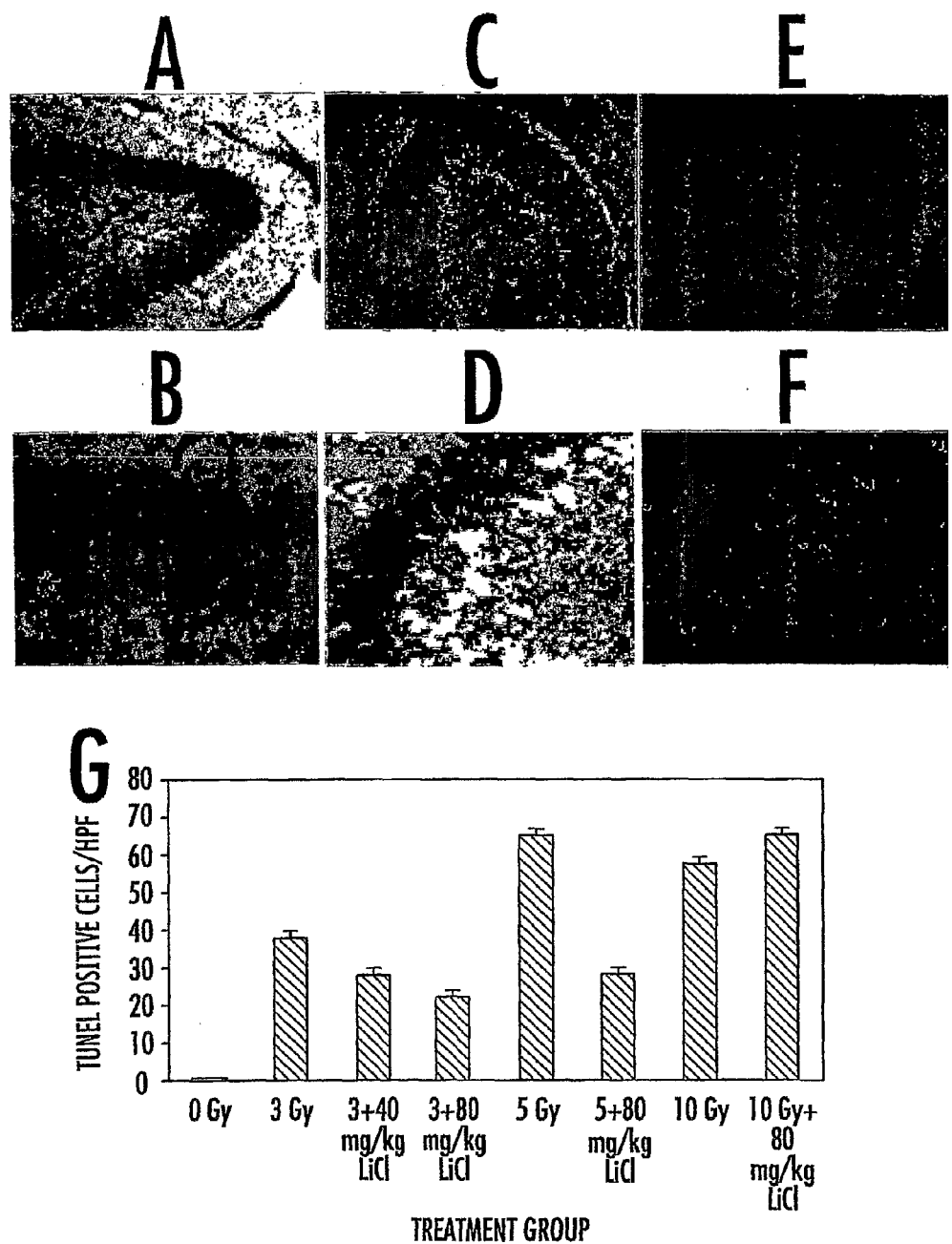
FIGS. 4A-4G depict the results of treating one-week-old Sprague-Dawley rats pups with daily IP injections of lithium chloride (80 mg/kg) or PBS. On the $7^{th}$ day, the animals were treated with the indicated dose of cranial radiation. 10 hours later, the animals were sacrificed. Their brains were immediately removed, fixed, embedded, and sectioned coronally. Sections that contained hippocampus were stained by the TUNEL method; hematoxylin was used as a counterstain. Depicted are photomicrographs of rat hippocampus treated with 0 Gy at 100× (FIG. 4A) and 400× (FIG. 4B), 5 Gy at 100× (FIG. 4C) and 400× (FIG. 4D), and 5 Gy+lithium at 100× (FIG. 4E) and 400× (FIG. 4F). Examples of TUNEL-positive cells are illustrated with arrows. For each experimental group, three animals were evaluated. For each animal, at least three HPFs in the subgranular zone of the hippocampus were counted for TUNEL-positive staining cells.

The results are shown in FIGS. 4A-4F, and summarized in FIG. 4G. SGZ neurons stained positive with TUNEL stain in the irradiated brains but not in animals treated with 0 Gy. Treatment with 80 mg/kg of LiCl for 7 days resulted in a two-fold decrease in apoptosis at 5 Gy, but there was no significant reduction in apoptosis at 10 Gy. At this dose, lithium caused a decrease in weight gain and eventual weight loss by day seven. At a higher dose (160 mg/kg), lithium was uniformly fatal.

Example 6

LiCl Increases Inhibitory Phosphorylation of GSK3β and Increases Bcl-2 Expression In Vitro Lithium has a dual inhibitory action on GSK3β, including competitive inhibition of magnesium as well as inhibition of an activating phosphatase (Nonaka et al., 1998). To determine whether lithium treatment increases phosphorylation of GSK3β in hippocampal neurons, protein was extracted from treated and untreated HT-22 cells.

Figure 5:
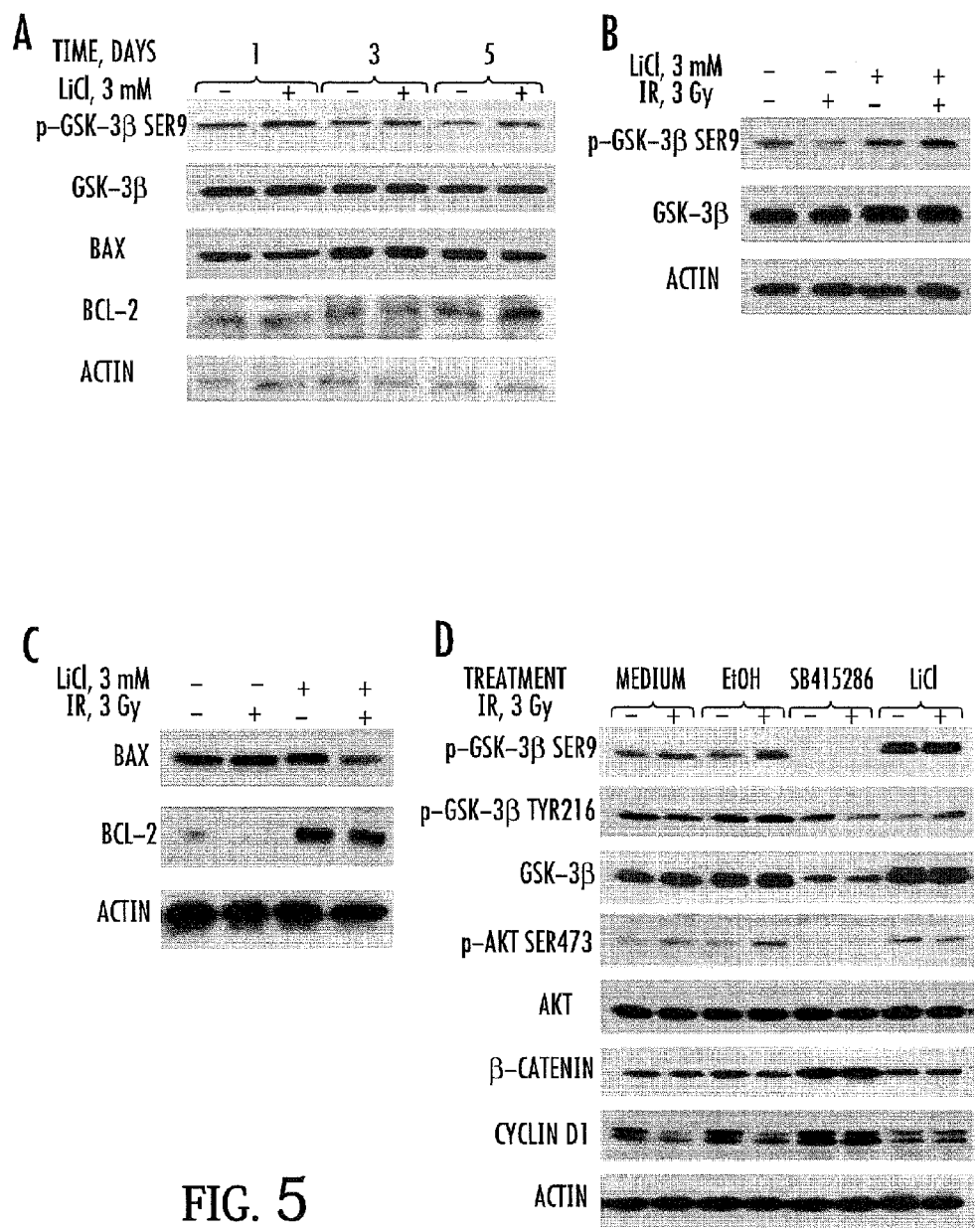
FIGS. 5A-5D depict the effects of GSK3β inhibitors on targets of the Akt/GSK3β signaling pathway in HT-22 mouse neuronal cells.

Western immunoblotting with antibody specific for phospho-GSK3β (Ser 9) is shown in FIG. 5A. Five days of 3 mM LiCl treatment increased phosphorylation of GSK3β at Ser 9 in HT-22 cells, indicating inhibition of GSK3β kinase activity. FIG. 5B shows that increased inhibitory phosphorylation of GSK3β at Ser 9 was sustained following irradiation of LiCl treated neuronal cells.

Microarray analysis of 30,000 mouse genes in HT-22 neuronal cells was studied after seven days of LiCl treatment. Gene expression was compared to that in cells treated with PBS alone. Several dozen genes showed a greater than two-fold increase and several dozen genes showed a greater than two-fold reduction in expression following LiCl treatment.

Bcl-2 is an anti-apoptotic signaling molecule that inhibits the pro-apoptotic factor Bax through heterodimerization (Jope, 2003). Bax function is required for radiation-induced apoptosis in the hippocampus Chen and Chuang, 1999). Lithium has been shown to increase levels of Bcl-2 and decrease levels of Bax. To determine whether lithium treatment alters expression of Bcl-2 and Bax in irradiated hippocampal neuronal cells, protein was extracted from treated and untreated HT-22 cells. Five days of 3 mM LiCl increased the expression of Bcl-2, while levels of Bax remained unchanged (see FIG. 5A). The high level of Bcl-2 was sustained after irradiation of LiCl pretreated HT-22 cells (see FIG. 5C). In the same cells, expression of Bax was significantly decreased in irradiated cells with LiCl treatment as compared to untreated cells (see FIG. 5C).

Example 7

Behavioral Modification in Memory Damage Induced by Radiotherapy is Attenuated by Lithium Cranial irradiation in newborn rodents is associated with severe spatial navigation deficits (Czurko et al., 1997). These deficits can be accounted for by radiation-induced apoptosis in the SGZ. To determine if lithium treatment could attenuate these deficits, C57BL/6 mice were treated with daily IP injections of 40 mg/kg LiCl. On postnatal day 14, the mice were irradiated with 7 Gy. Six weeks later, the animals were subjected to Morris Water Maze testing.

Figure 6A:
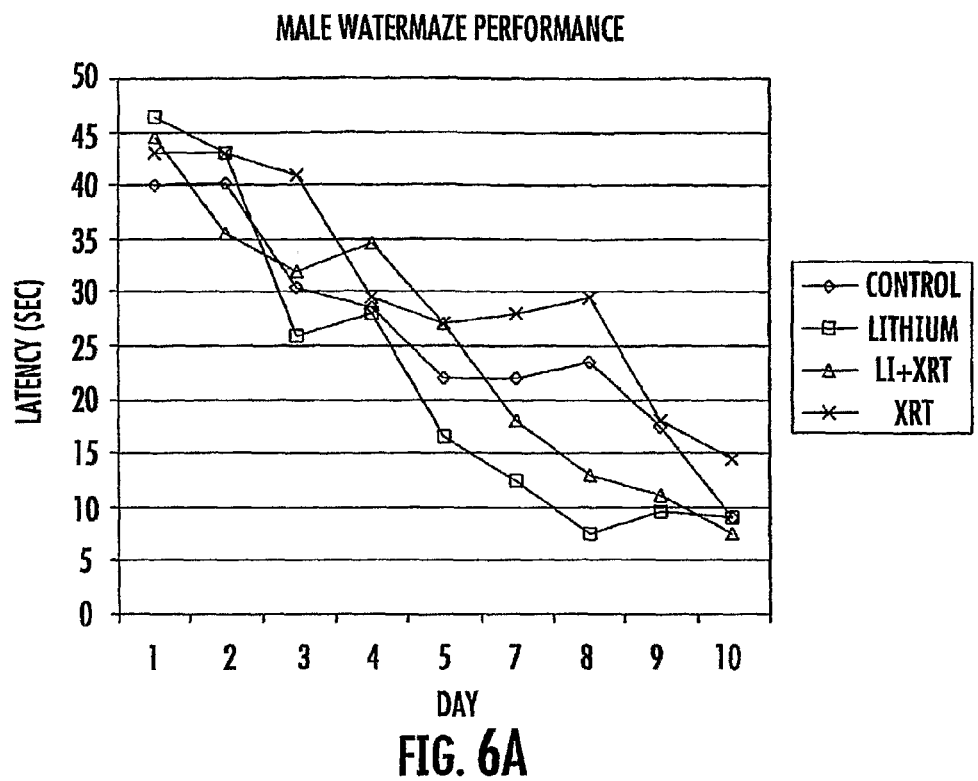
FIGS. 6A and 6B depict lithium-attenuated disruption of learning as measured via the Morris water maze test in male (FIG. 6A) and female (FIG. 6B) mice. Lithium (Li) and/or exposure to ionizing radiation (XRT) was administered to mice as indicated.
Figure 6B:
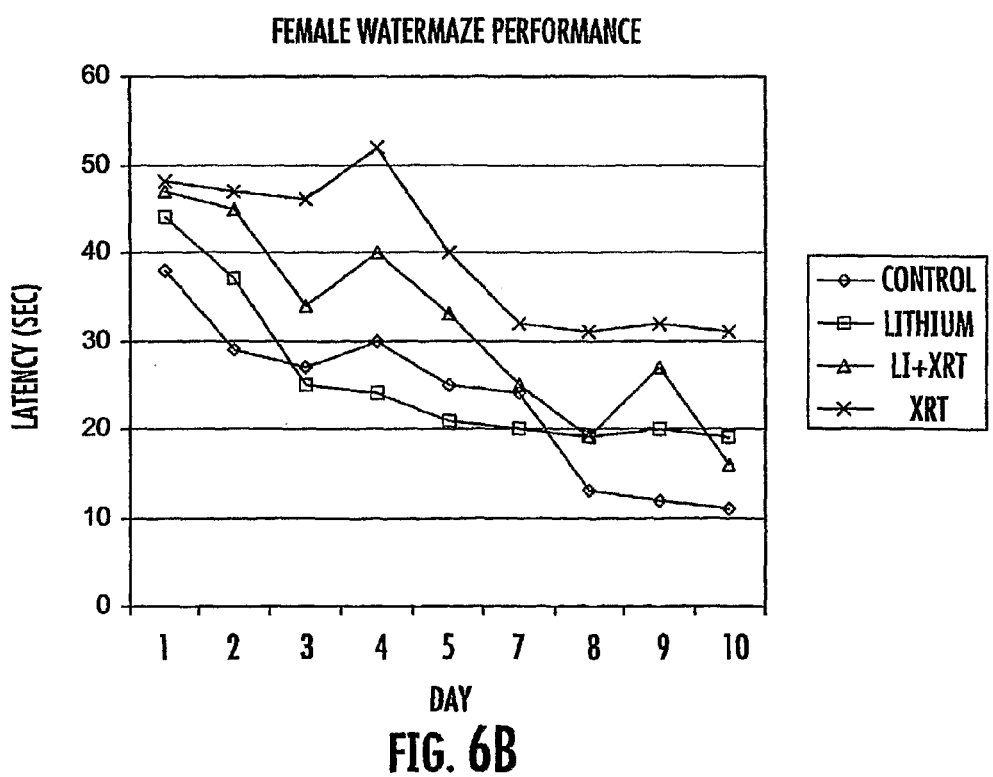
Figure 7A:
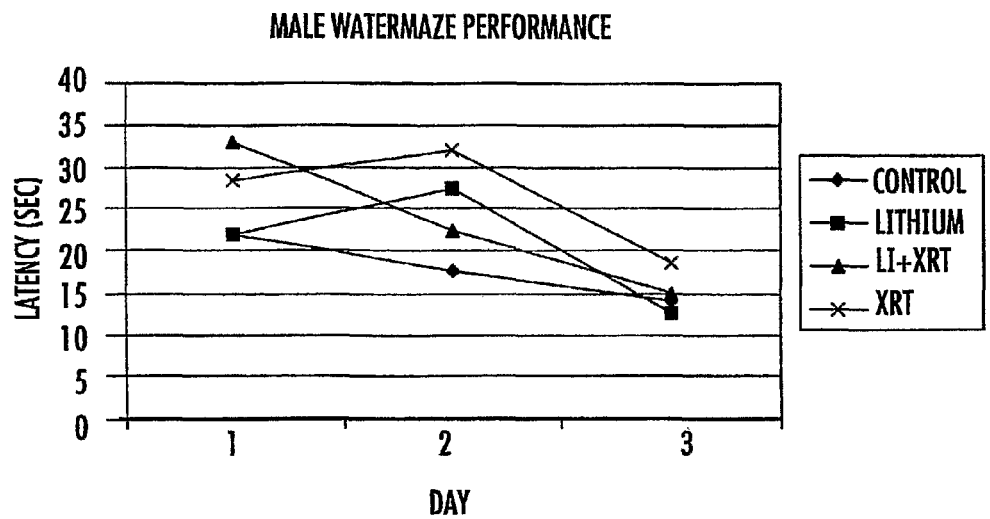
FIGS. 7A and 7B depict lithium-attenuated disruption of learning as measured via the visible platform test in male (FIG. 7A) and female (FIG. 7B) mice. Lithium (Li) and/or exposure to ionizing radiation (XRT) was administered to mice as indicated.
Figure 7B:
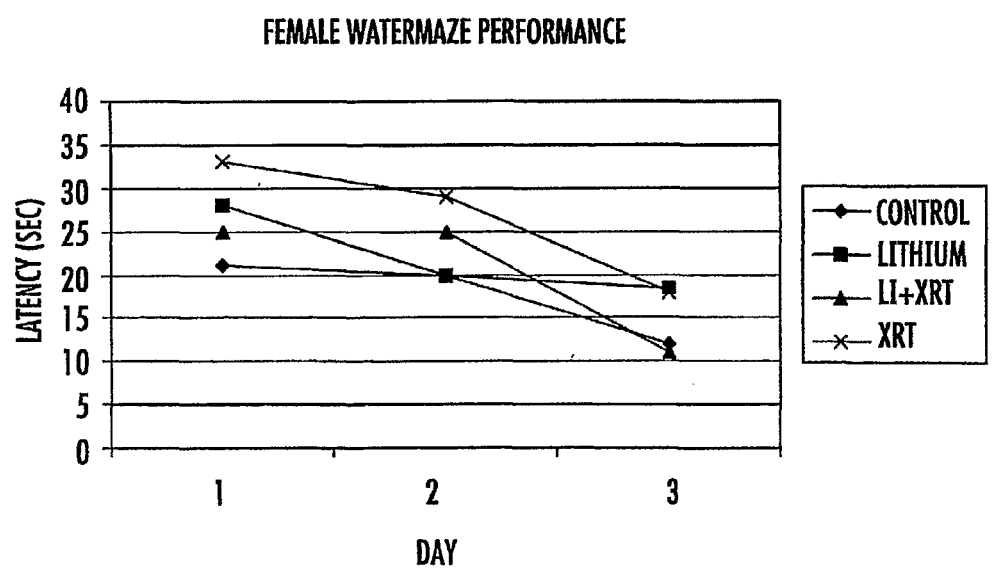

When animals were exposed to ionizing radiation, animals treated with lithium showed improvements in memory as measured via the Morris Water Maze test (FIGS. 6A-6B). Additionally, lithium attenuated memory destruction caused by ionizing radiation as measured via the visible platform test (FIGS. 7A-7B).

Figure 8:
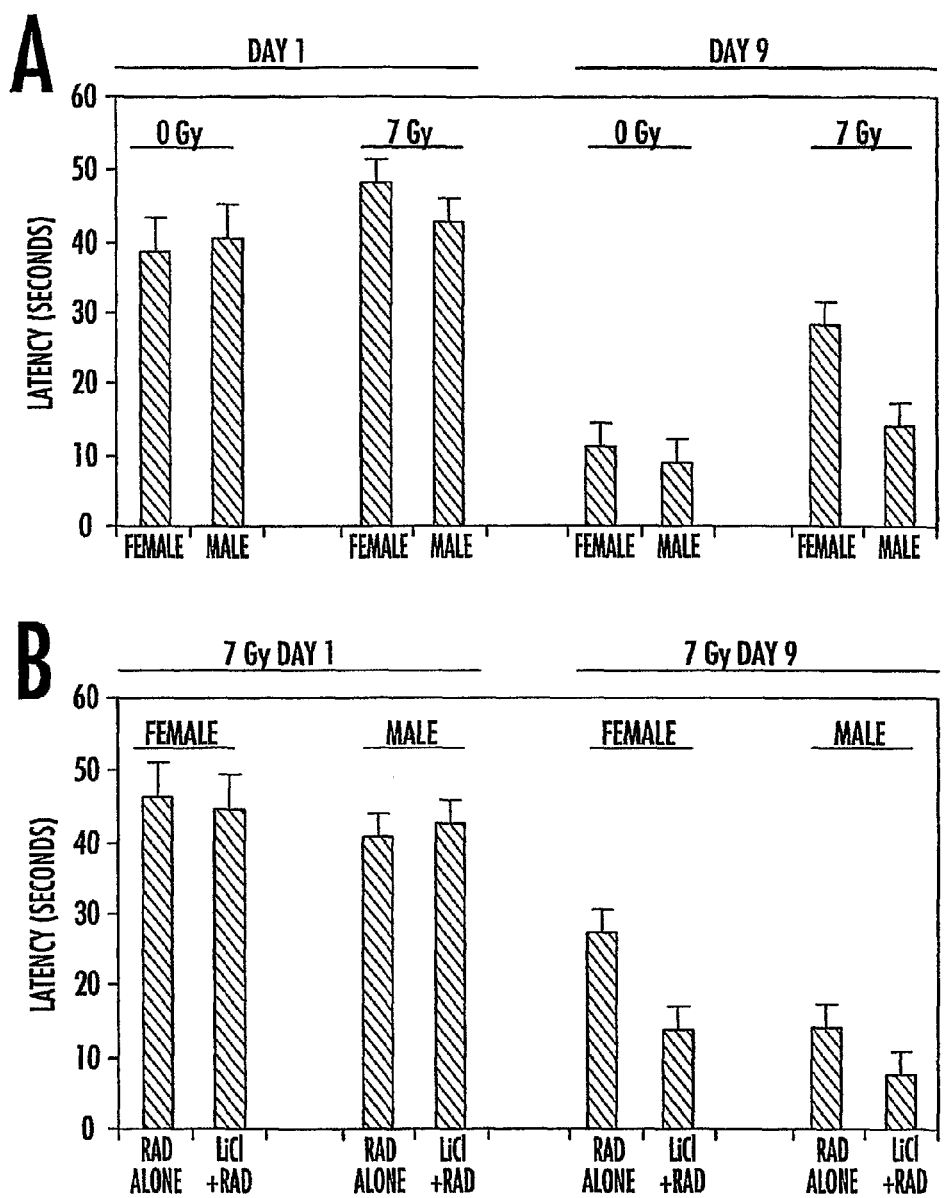
FIG. 8 presents bar graphs that demonstrate that lithium improves cognitive function following cranial irradiation. One-week-old C57BL/6 mice were treated with daily i.p. injections of LiCl (40 mg/kg) or PBS for seven days. On the 7th day, the pups were then treated with 7 Gy of cranial irradiation or sham irradiation. Six weeks later, the animals were studied using the hidden Morris Water Maze testing. Shown here are bar graphs of the average latencies (+/−SEM) of unirradiated vs. irradiated male or female mice on days 1 and 9 (FIG. 8A), and irradiated vs. irradiated after lithium treatment male or female mice on days 1 and 9 (FIG. 8B).

It was observed that female mice were particularly debilitated by irradiation, taking an average of twice as long to locate the hidden platform on the last day of testing as compared to their male littermates (28.1 vs. 14.6 seconds, FIG. 8A, p=0.027). This sex difference in radiation-induced neurocognitive dysfunction supports clinical findings that females are at increased risk for developing severe cognitive deficits as compared to their male counterparts. While all groups of mice achieved comparable latency times on the first day of training, significantly lower latency times were observed after nine days of learning in mice treated with lithium prior to radiation as compared to animals treated with radiation alone (FIG. 8B, p=0.02 for both males and females).

Discussion of Examples 1-7

Disclosed herein is the discovery that lithium chloride treatment (3 mM) for seven days, but not 24 hours, increased clonogenic survival of hippocampal neuron cells in culture.

Without wishing to be bound by any particular theory of operation, this finding can be explained in several ways. First, modulation of transcription is likely required for lithium's neuroprotective effect. GSK3β is known to inhibit a number of crucial transcription factors involved in cell survival and proliferation, including cyclic AMP response element binding protein (CREB; Grimes and Jope, 2001), heat shock factor 1 (HSF-1; Bijur and Jope, 2000), and activator protein-1 (AP-1; Boyle et al., 1991). CREB has been shown to increase expression of the anti-apoptotic protein bcl-2. HSF-1 is activated in response to many stressors (including radiation) and controls the expression of protective heat shock proteins. AP-1 regulates the expression of a number of genes involved in cell survival and proliferation.

Disclosed herein is the discovery that 7 days of lithium treatment enhanced survival of hippocampal neurons in vitro, but one day was not effective. Without wishing to be bound by any particular theory of operation, these findings suggested that downstream modulation of protein expression might be required to manifest lithium's neuroprotective effect.

Introduction To Examples 8-13

Protein Kinase B (PKB/Akt)-dependent Glycogen Synthase Kinase 3β Phosphorylation In Irradiated Vascular Endothelium The vascular endothelium plays a critical role in the response to ionizing radiation (Paris et al., 2001; Garcia-Barros et al., 2003). The physiologic response of microvasculature to ionizing radiation is in part dependent upon signaling through PI3K (Edwards et al., 2002; Geng et al., 2004; Tan and Hallahan, 2003). Overexpression of the mutant p85 component of PI3K enhances radiation-induced apoptosis and minimizes capillary tubule formation (Tan and Hallahan, 2003).

The PI3K/Akt signal transduction pathway has been implicated in survival signaling in various cell types (Brazil and hemmings, 2001; Datta et al., 1999; Lawlor and Alessi, 2001; Testa and Bellacosa, 2001; Vivanco and Sawyers, 2002). In endothelial cells, PI3K/Akt can be activated through a family of receptor tyrosine kinases that are activated by growth factors (Burgering and Coffer, 1995; Mazure et al., 1997). PI3K, the downstream effector of RTKs, has been shown to be a molecular target for enhancement of the radiation response in tumor endothelium (Edwards et al., 2002; Mandriota and Pepper, 1997; Tan and Hallahan, 2003). For example, Akt signaling participates in angiogenesis following VEGF stimulation of endothelial cells and regulates capillary-like tubule formation (Gerber et al., 1998). Akt can be activated independently of growth factor or PI3K signaling (Bianco et al., 2003). Recently, it has been shown that radiation induces phosphorylation of Akt within endothelial cells (Tan and Hallahan, 2003). These studies suggest that Akt can be a molecular target for the development of drugs that enhance the efficacy of cancer therapy.

The results demonstrating the role of Akt in endothelial cell viability led to questions about how this signal transduction pathway contributes to the vascular response to ionizing radiation. Although high dose irradiation exceeds the threshold for radiation-induced apoptosis in the endothelium (Garcia-Barros et al., 2003; Paris et al., 2001), lower doses do not induce programmed cell death (Geng et al., 2004; Schueneman et al., 2003). It appeared that low dose irradiation activates the Akt-mediated cell viability pathway, which is in part dependent upon phosphorylation of down stream GSK3β (Mao et al., 2001; Rossig et al., 2002). PI3K-induced activation of Akt results in phosphorylation of GSK3β, which in turn inhibits GSK3β enzymatic activity (Kotani et al., 1999; Pap and Cooper, 1998; Salas et al., 2003). Thus, disclosed herein is a role of Akt and GSK3β in endothelial cell survival during low dose irradiation.

GSK3β is a ubiquitously expressed protein-serine/threonine kinase that was initially identified as an enzyme that regulates glycogen synthesis in response to insulin (Eldar-Finkelman et al., 1996; He et al., 1998; Pap and Cooper, 1998; Salas et al., 2003). Stimulation of cells with insulin causes inactivation of GSK3β through a PI3K/Akt-dependent mechanism (Summers et al., 1999). GSK3β participates in multiple cellular processes including cell growth, differentiation, cell survival, and cytokinesis (Doble and Woodgett, 2003; Pap and Cooper, 2002; Sanchez et al., 2003).

Interestingly, GSK3β has emerged as a regulator of neuronal, endothelial, hepatocyte, fibroblast, and astrocyte death (Pap and Cooper, 2002; Sanchez et al., 2003). Direct overexpression of GSK3β is known to induce apoptosis in various cells in culture, and specific inhibitors of GSK3β are able to ameliorate this apoptotic process (Culbert et al., 2001; Hetman et al., 2000; Pap and Cooper, 1998; Pap and Cooper, 2002; Tong et al., 2001; Sanchez et al., 2003; Hongisto et al., 2003; Schwabe and Brenner, 2002; Kim et al., 2002; Watcharasit et al., 2002).

Akt is a key effecter of the PI3K survival pathway and enhances cell survival by minimizing the induction of apoptosis (Burgering and Coffer, 1995; Pap and Cooper, 1998; Sanchez et al./, 2003). The purpose of the studies described herein was to more directly test the role of Akt and GSK3β in the response of the endothelium to ionizing radiation.

Phosphorylation of Akt and GSK3β occurred within minutes of irradiation of endothelial cells with 1 to 2 Gy. To determine whether Akt contributes to the response of microvasculature to ionizing irradiation, endothelial cells were transduced with adenovirus vectors containing a mutant Akt (T308A, S473A) genetic construct (Luo et al., 2000). This inactive mutant Akt is not activated by phosphorylation (Jetzt et al., 2003; Luo et al., 2000). The Akt dominant negative genetic construct enhanced radiation-induced apoptosis and prevented capillary tubule formation. Overexpression of dominant negative GSK3β can protect cells from programmed cell-death (Sanchez et al., 2003). The GSK3β dominant negative genetic constructs eliminated this effect of Akt antagonists on irradiated endothelial cells. The results indicated that inactivation of Akt-mediated signal transduction eliminated endothelial cell resistance to low dose irradiation.

Materials and Methods Used in Examples 8-13

Adenovirus vectors and other reagents. The adenovirus vector encoding a dominant-negative mutant of Akt was obtained from Dr. K. Walsh (Luo et al., 2000). The dominant-negative mutant GSK3β was a gift from Dr. M. J. Birnbaum (Summers et al., 1999). The adenovirus vector encoding GFP was purchased from Clontech Laboratories Inc. (Mountain View, Calif., United States of America). Lithium was obtained from Sigma. GSK3β inhibitor III and caspase-3 cellular activity assay kits were purchased from CALBIOCHEM® (a division of EMD Biosciences, Inc., San Diego, Calif., United States of America). Akt tyrosine kinase inhibitor, ALX-349, was purchased from ALEXIS® Biochemicals (a division of AXXORA, LLC, San Diego, Calif., United States of America). Viruses were propagated in HEK-293 cells, purified by column chromatography, quantitated, and dosed by particle yield. For adenovirus transduction of HUVEC, $8 \times 10^5$ cells, cultured in 100 cm plates were transduced with adenovirus vector at 10-100 plaque-forming units/cell.

Cell culture. Primary culture vascular endothelial cells pooled from multiple donors (HUVEC) were obtained from CLONETICS® (a division of Cambrex Bioscience Inc., Baltimore, Md., United States of America) and were maintained in EBM-2 medium supplemented with EGM-2. 4-5 passage cells were used in this study. HEK-293 cells were cultured in DMEM medium from Invitrogen Corp. (Carlsbad, Calif., United States of America). All culture media were supplemented with 20 µg/ml streptomycin. More than 90% of the HUVEC transduced at a similar multiplicity of infection with an adenovirus expressing GFP served as control vector. Transduced cells were subjected to further treatment 24 hours late. An Eldorado 8 Teletherapy $^{60}$Co Unit (Atomic Energy of Canada Limited, Mississauga, Ontario, Canada) was used to irradiate endothelial cell cultures at a dose rate of 0.84 Gy/min. Delivered dose was verified by using thermoluminescence detectors.

Apoptosis quantitation. Apoptosis was analyzed by caspase 3 cleavage and propidium iodide staining. Morphologic analyses of primary culture endothelial cells apoptosis were performed under microscope using propidium iodide staining. Apoptotic cells were identified according to their nuclear condensation and fragmentation. Briefly, HUVEC were transduced with adenovirus for 24 hours. Transduced cells were irradiated with 3 Gy. Cells were washed with PBS several times at 24 hours after treatment, and then permeabilized with 30% methanol and stained with propidium iodide in PBS. Apoptotic and non-apoptotic cells were counted in multiple randomly selected fields, and data were presented as percentage of cells that were apoptotic. Student's test was used to analyze statistical difference. A P value of 0.05 or less was considered statistically significant.

Caspase-3 cellular activity. Caspase 3 activity was assessed according to the CALBIOCHEM® protocol. Cells were grown to 80% confluence and then treated with GSK3β inhibitors and/or radiation. Cells were then washed twice with PBS and collected by trypsinization followed by centrifugation. The cells were lysed in the lysis buffer and incubated on ice for 10 minutes. Lysates were centrifuged for 10 minutes at 12,000 rpm, and the supernatants were added to microcentrifuge tubes containing caspase activity assay buffer. Caspase substrate was added to each sample and incubated for 2 hours at room temperature. Caspase enzyme activity was detected at 405 nm.

Immunoblot analysis. HUVEC were treated at indicated times prior to protein extraction and whole cell extracts were prepared as previously described (Edwards et al., 2002; Schueneman et al., 2003). Protein concentration was quantified by the Bio-Rad method. For the analysis of caspase 3 cleavage, 40 µg of whole cell extract were loaded onto a 12% SDS acrylamide gel and analyzed as previously described (Geng et al., 2004; Schueneman et al., 2003). For the detection of GSK3β, 20 µg of whole cell extracts were loaded onto an 8% SDS acrylamide gel and transferred onto nitrocellulose membranes. The membrane was blocked with PBS containing 5% dry milk and incubated with primary antibody overnight at 4° C. After three washes with PBS, the blocking buffer was re-added to the membrane and incubated with secondary antibody for 1 hour at room temperature. ECL (Amersham Biosciences) was used for detection. The primary antibodies for caspase 3 and GSK3β were purchased from Cell Signaling Technology, Inc. (Beverley, Mass., United States of America); the second antibody was purchased from Santa Cruz Biotechnology, Inc. (Santa Cruz, Calif., United States of America).

Cell migration assay. Primary culture endothelial cells were grown to 75% confluence in 100 mm dishes and transduced with dominant negative Akt adenovirus or a control, Ad.GFP, adenovirus. 24 hours later, the transduced HUVEC were irradiated with 3 Gy, then washed with PBS and dissociated from dishes by trypsin buffer. HUVEC, $1 \times 10^5$, were placed into Fibronectin-Coated Boyden Chamber at 37° C. for 6 hours. The filter was carefully removed and cells attached on upper side were wiped off by cotton-tips. The HUVEC migrating through the filter and appearing on the lower side were fixed by careful immersion of the filter into 70% ethanol for 15 minutes and stained. Cells were washed with PBS, and detached from the filter with dissociation buffer. The number of migrated cells was detected by measuring the Optical Density (at 550 nm) of cell-dissociation buffer. Each experiment was performed in duplicate, and three separate experiments were performed for each group. Student's test was used to analyze statistical differences.

Capillary-like network formation in MATRIGEL™ Basement Membrane Matrix. A 10 mg per ml mixture of MATRIGEL™ Basement Membrane Matrix (200 µl of 10 mg/ml mixture, BD Bioscience, Bedford, Mass., United States of America) was placed in each well of an ice-cold 24-well plate. The plate was allowed to sit at room temperature for 15 minutes then incubated at 37° C. for 30 minutes to allow the MATRIGEL™ Basement Membrane Matrix to polymerize. HUVEC were then seeded at $5 \times 10^5$ into each MATRIGEL™ Basement Membrane Matrix-coated well. The cells were incubated for 24 hours to allow capillary-like structure formation. For ease of handling and optimal visualization of the capillary-like network, medium was removed carefully after incubation, and agarose was gently added to the cells. After solidification of the agarose, immobilized tubes were fixed and stained with Diff-Quik solution. The tubules were counted under microscopy and recorded. Student's test was used to analyze statistical differences.

In vivo assays of microvascular response. The formation of new microvasculature was studied in mouse models using both the dorsal skin fold tumor vascular window and capillary-like tubule formation models. Capillary formation in the irradiated mouse utilized 10 ml MATRIGEL™ Basement Membrane Matrix with a 5 ml solution of heparin (1 µg/ml) and VEGF (1 µg/ml). Adenovirus vectors containing dominant negative genetic constructs of mutant Akt or GSK3 were added to MATRIGEL™ at $2 \times 10^8$ PFU/500 µl. Virus laden MATRIGEL™ Basement Membrane Matrix (500 µl) was then injected subcutaneously into the flank of C57BL/6 mice. The flank was then irradiated with 3 Gy of superficial x-rays. FITC-dextran was injected by tail vein 72 hours later and mice were euthanized 30 minutes later. The FITC-dextran containing endothelium within the MATRIGEL™ Basement Membrane Matrix plug was imaged by fluorescence microscopy. Capillaries were counted from three mice and Student's test was used to analyze statistical differences.

The dorsal skin fold window was a 3 g plastic frame applied to the skin of the mouse before tumor implantation and remains attached for the duration of the study. The chamber was screwed together, while the epidermis was incised and remained open with a plastic covering. The midline was found along the back, and a clip was placed to hold the skin in position. The epidermis of the four flaps was then removed using a scalpel with an effort to follow the hypodermis superior to the fascia. The bottom portion of the chamber was put in place, and the top was carefully positioned on the cut side so that the window and the circular incision were fitted. Animals were placed under a heating lamp for several days. Microvasculature within the window was monitored by microscopy. Blood vessels developed in the dorsal skin fold window within 1 week of implantation of Lewis lung carcinoma cells. Microvascular windows were treated with 2 Gy of superficial X-rays using 80 kVp (Pantak X-ray Generator). Five mice were studied in each of the treatment groups. ALX-349 (25 mg/kg) was injected i.p. 30 minutes before irradiation. The window frame was marked with coordinates, which were used to photograph the same microscopic field each day. Vascular windows were photographed using a 4× objective to obtain a 40× total magnification. Color photographs were used to catalogue the appearance of blood vessels on days 0-7. Photographs were scanned into Photoshop software, and vascular centerlines were positioned by IMAGEPR™ software and verified by an observer blinded to the treatment groups. Tumor blood vessels were quantified by the use of IMAGEPR™ software, which quantifies the vascular length density of blood vessels within the microscopic field. The mean and standard error of the mean of vascular length density for each treatment group were calculated, and variance was analyzed by student's test. A P value of 0.05 was considered statistically significant.

Example 8

Akt-dependent Phosphorylation of GSK3β in X-irradiated Endothelium

Figure 9:
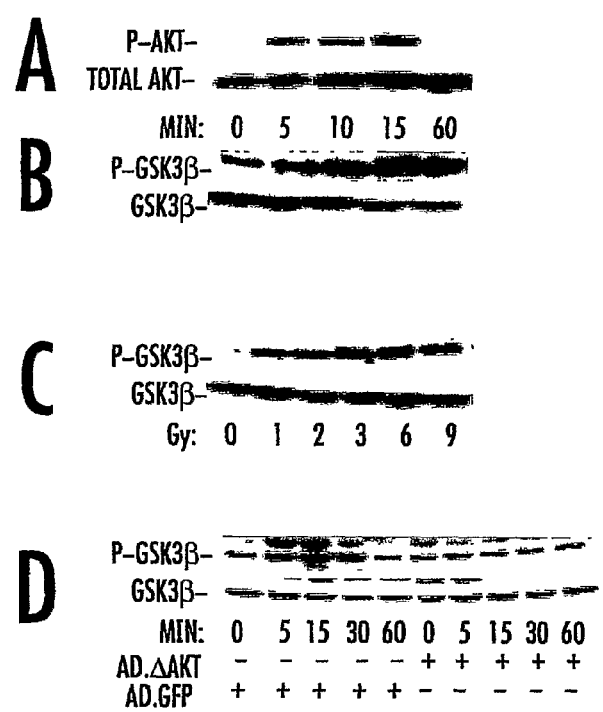
FIGS. 9A-9D depict Akt and GSK3β phosphorylation in irradiated endothelial cells. HUVEC were treated with 3 Gy and total protein was extracted at the indicated time points following irradiation.

To study radiation-induced Akt phosphorylation, endothelial cells were irradiated with 3 Gy and total protein was extracted at the indicated times (see FIG. 9A). Western immunoblots were probed with antibodies specific for phosphorylated Akt and total Akt. Phosphorylation of Akt was minimal in untreated control cells, but phosphorylation increased within 5 minutes and maximal phosphorylation occurred at 15 minutes after irradiation.

Because GSK3β is one of the key effectors of Akt signaling, radiation might also lead to phosphorylation of GSK3β. To study radiation-induced GSK3β phosphorylation, endothelial cells were irradiated with 3 Gy and total protein was extracted at the indicated times (see FIG. 9B). Western immunoblots were probed with antibodies specific for phosphorylated GSK3β and total GSK3β. Minimal phosphorylation of GSK3β was found in untreated control cells. Increased phosphorylation was first noted at 5 minutes and maximal phosphorylation occurred at 15 minutes.

To further characterize radiation induced phosphorylation of GSK3β, endothelial cells were treated with varying radiation doses. Radiation-induced phosphorylation of GSK3β was dose dependent, requiring as little as 1 Gy. Maximal phosphorylation was observed in response to 3 Gy (see FIG. 9C).

To determine whether Akt participates in phosphorylation of GSK3β following irradiation, a dominant negative Akt genetic construct was overexpressed in primary culture vascular endothelial cells. Total protein was extracted from endothelial cells at the indicated time points after irradiation. Overexpression of dominant negative Akt abrogated phosphorylation of GSK3β following irradiation (see FIG. 9D). In comparison, cells transduced with control vector Ad.GFP showed no interruption of radiation-induced GSK3β phosphorylation (see FIG. 9D).

Example 9

Akt Dominant Negative Induces Apoptosis in Irradiated Endothelium

Figure 10:
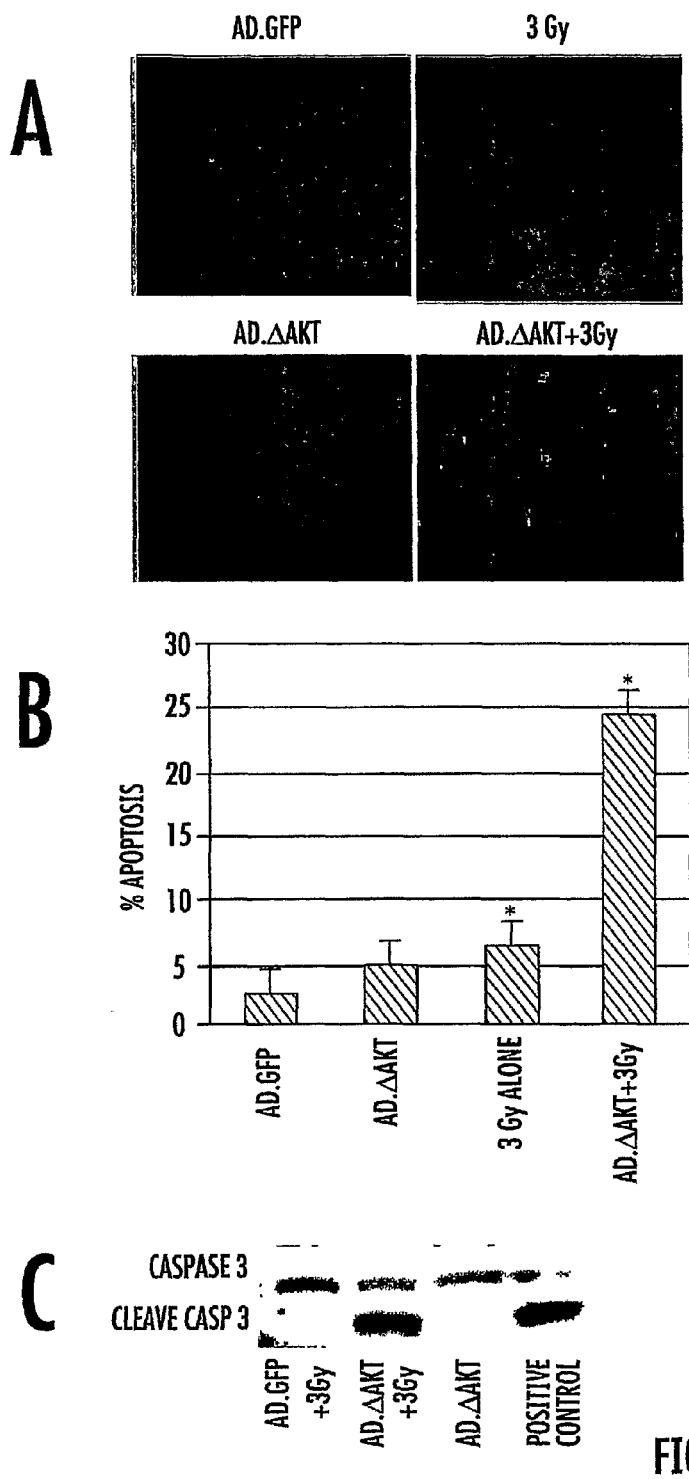
FIGS. 10A-10C depict apoptosis in endothelial cells. HUVEC were treated with Ad.ΔAkt or Ad.GFP and irradiated with 3 Gy or 0 Gy as indicated.

To determine whether Akt contributes to the response of microvasculature to ionizing irradiation, endothelial cells were transduced with adenovirus vectors containing the mutant Akt (T308A, S473A) genetic construct. The inactive mutant Akt is not activated by phosphorylation (Jetzt et al., 2003; Luo et al., 2000). FIGS. 10A-10C show that 5% of primary culture endothelial cells undergo apoptosis following treatment with dominant negative Akt as compared to 2.5% in the control cells. In comparison, when irradiated, the dominant negative Akt-transduced cells had markedly increased the percentage of apoptotic cells to 25%, which was significantly increased as compared to treatment with the dominant negative Akt or with radiation alone (p<0.001; FIGS. 10A-10C).

Western blot analysis of caspase 3 activation was utilized to verify the induction of apoptosis. FIG. 10C shows that caspase 3 was cleaved in HUVEC transduced with dominant negative Akt following irradiation. In comparison, Ad.ΔAkt or 3 Gy alone resulted in minimal caspase 3 cleavage in endothelial cells. Caspase 3 activity was verified by activation of caspase 3-specific substrate, which confirmed results from western blot analysis that caspase enzyme activity was markedly increased when cells were transduced with an Akt dominant negative construct followed by irradiation. In comparison, cells treated with Ad.ΔAkt alone or radiation alone had minimal activation of caspase 3 enzyme activity. Overexpression of mutant Akt did not significantly affect primary culture endothelial cell viability but did enhance radiation-induced apoptosis.

Example 10

Endothelial Cell Migration and Tubule Formation Assays

Figure 11:
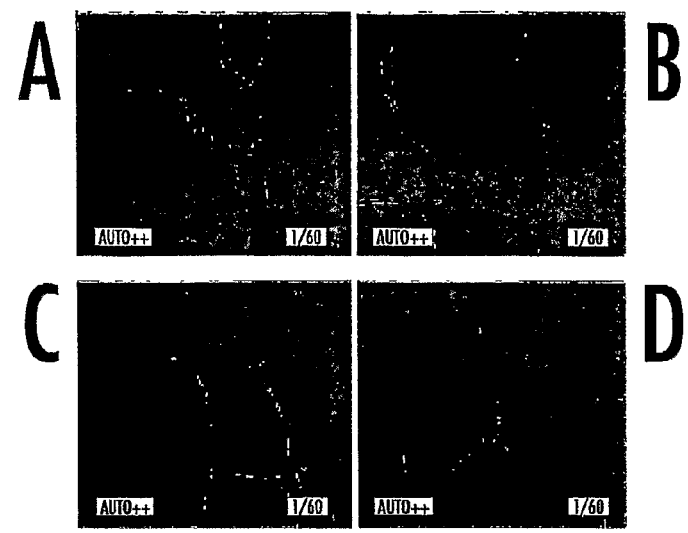
FIGS. 11A-11E depict endothelial cell migration and tubule formation.
Figure 11:
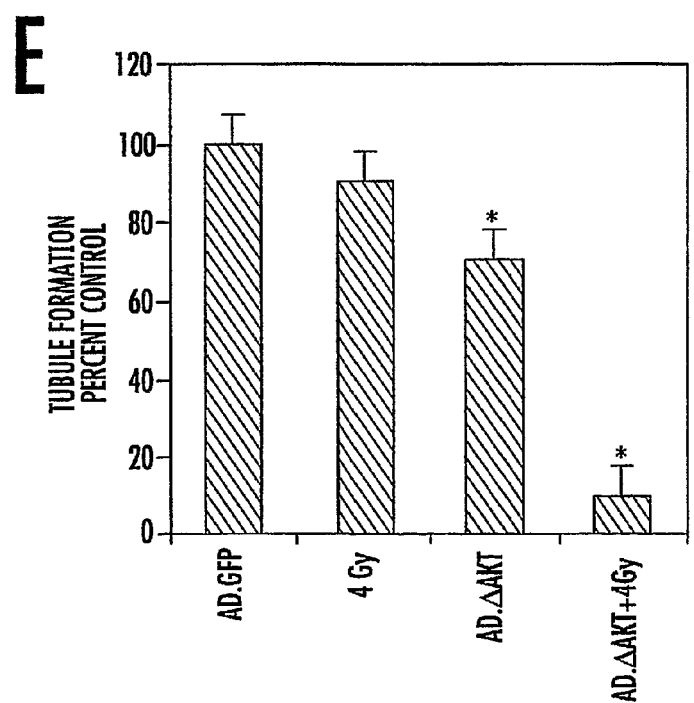
Figure 12:
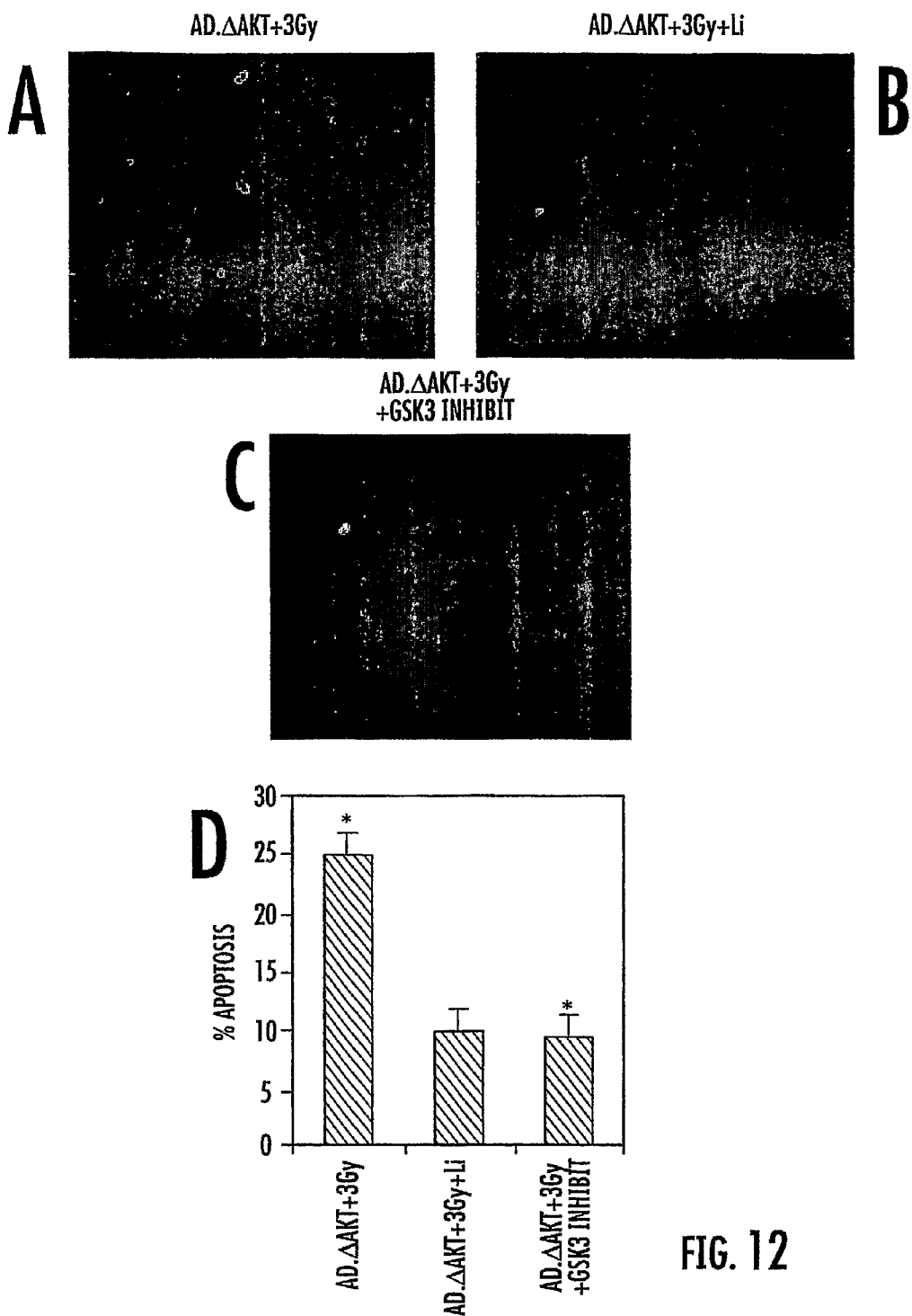
FIGS. 12A-12H depict attenuation of apoptosis by GSK3β inhibitors in HUVEC. HUVEC were transduced with Ad.Δ-Akt vector followed by irradiation by 3 Gy. The cells were pretreated with lithium (10 mM) or the GSK3β inhibitor (100 nM) for 1 hour prior to irradiation. Endothelial cells treated with Ad.ΔAkt were then treated with lithium. Endothelial cells were treated with ALX-349 following transduction with Ad.DN-GSK3. HUVEC were fixed and stained with propidium iodide at 24 hours after irradiation. Depicted are PI stained cells after treatment with Ad.ΔAkt plus 3 Gy (FIG. 12A), Ad.ΔAkt plus 3 Gy and lithium (FIG. 12B), and Ad.Δ-Akt with 3 Gy and GSK3β inhibitor (FIG. 12C).
Figure 12:
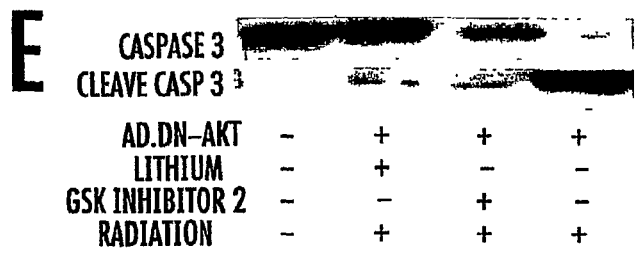
Figure 12:
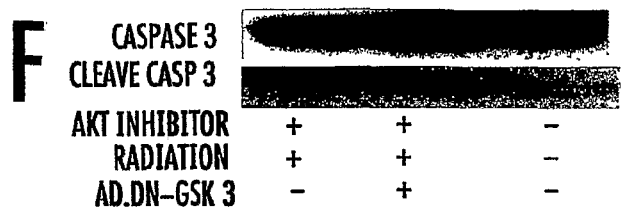
Figure 12:
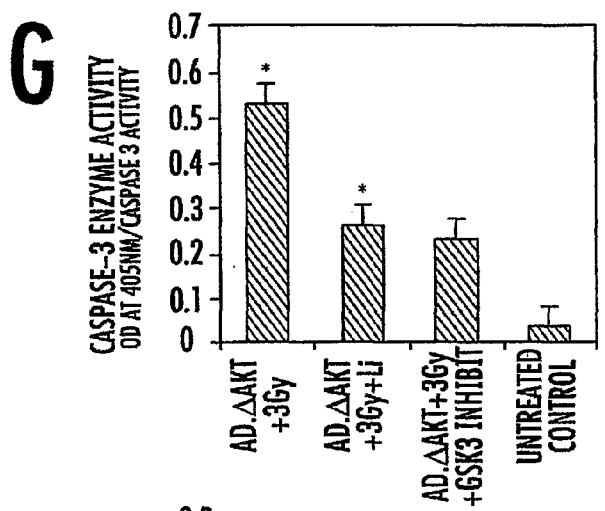
Figure 12:
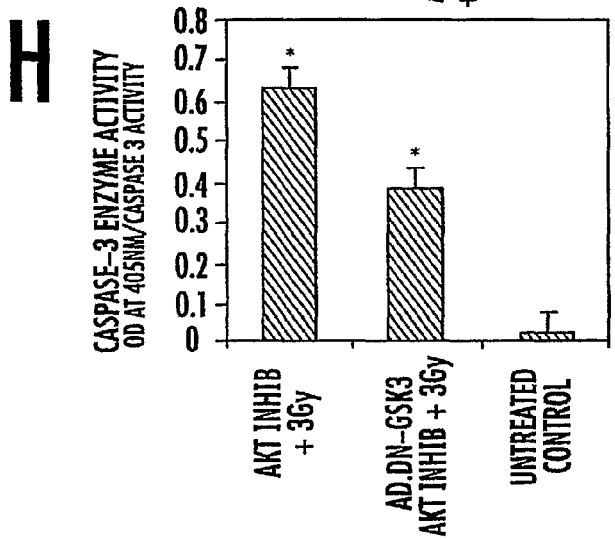

FIGS. 11A-11E depict endothelial cell migration and tubule formation. FIGS. 11A-11D depict capillary-tubule formation attenuation in irradiated endothelial cells by Ad.ΔAkt. HUVEC were transduced with Ad.ΔAkt or vectors and treated with 3 Gy or 0 Gy. Cells were immediately cultured onto MATRIGEL™ Basement Membrane Matrix. The formation of capillary-like structures was monitored for 24 hours. Depicted are representative photographs of capillary tubule formation 24 hours after treatment with Ad.GFP (FIG. 11A), Ad.ΔAkt alone (FIG. 11B), 3 Gy alone (FIG. 11C), or Ad.ΔAkt+3 Gy (FIG. 11D). The bar graph presented in FIG. 11E shows the mean and standard error of the mean of the three capillary formation experiments in MATRIGEL™ Basement Membrane Matrix. *P<0.01.

Example 11

Akt Regulates Capillary Tubule Formation in Irradiated Endothelium

To determine whether Akt is required for capillary tubule formation in irradiated vascular endothelium, a dominant negative Akt-transduced HUVEC plated onto MATRIGEL™ Basement Membrane Matrix was employed. HUVEC transduced with Ad.GFP control vector attached to MATRIGEL™ Basement Membrane Matrix when plated and formed capillary-like structures within 24 hours following irradiation. HUVEC containing dominant negative mutant Akt showed a reduction in the number of capillary-like tubules as compared to that of control and irradiated cells (FIGS. 12A-12H). In comparison, irradiated HUVEC overexpressing the dominant negative Akt showed significantly decreased number of capillary-like tubules, while irradiated cells transduced with Ad.GFP showed no reduction in capillary formation. Primary culture endothelial cells transduced with dominant negative Akt and treated with radiation (3 Gy) lost the ability to form capillary-like tubules. These data indicated that Akt signaling contributed to endothelial capillary tubule formation following irradiation.

Example 12

GSK3β Antagonists Prevent Apoptosis in Endothelial Cells

To determine whether dominant negative GSK3β can protect endothelial cells from programmed cell-death induced by a dominant negative Akt and radiation, caspase 3 activity and propidium staining was investigated. These experiments showed that a dominant negative GSK3β prevented apoptosis. HUVEC were transduced with a dominant negative GSK3β and transduced cells were then treated with an Akt inhibitor and radiation. As shown in FIGS. 12A-12H, a dominant negative GSK3β decreased caspase 3 activity in irradiated endothelial cells treated with Akt inhibitor. In comparison, cells treated with the AD.GFP control vector should increase caspase 3 cleavage following treatment with Akt inhibitor and radiation (FIGS. 12A-12H).

In a separate experiment, whether lithium, a GSK3 inhibitor, could protect endothelial cells from cell death induced by dominant negative Akt and irradiation was investigated (FIGS. 12A-12H). To determine whether LiCl alters endothelial response to therapy, HUVEC were grown to 80% confluence and transduced with a dominant negative Akt-encoding adenovirus. Cells were treated with lithium at 10 mM for 2 hours and then irradiated with 3 Gy. Twenty four hours later, total cellular protein was extracted. As shown in FIGS. 12A-12H, lithium significantly protected endothelial cells from apoptosis induced by radiation and dominant negative Akt expression, and had significantly decreased caspase 3 activity compared to untreated control cells.

Example 13

GSK3β Antagonists Improve Endothelial Function

Figure 13:
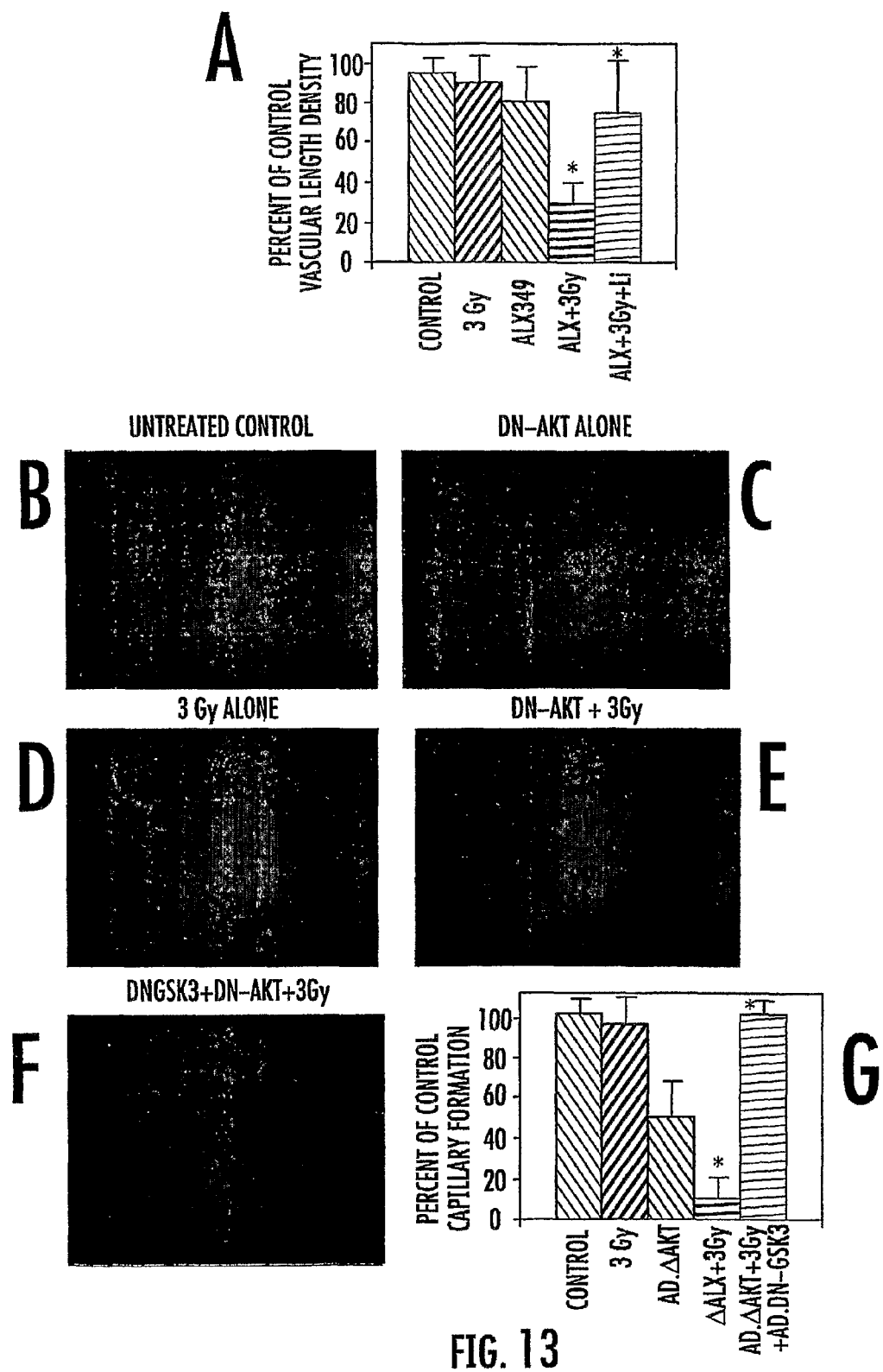
FIGS. 13A-13G depict improved endothelial function resulting from GSK3β antagonist treatment. Tumor angiogenesis was monitored by microscopy using the dorsal skin fold window implanted with LLC tumors. Mice were randomly assigned to 4 treatment groups that included un-treated control, ALX-349 alone, 3 Gy alone, and ALX-349 plus 3 Gy. The tumor vascular window was treated with 3 Gy of superficial x-rays. The changes in the microvasculature were monitored by microscopy at the indicated time points. Vascular length density of tumor blood vessels was measured by use of Image Pro software analysis of digital images.

To determine whether Akt inhibition has an impact upon tumor vascular response to radiation, the Akt inhibitor ALX-349 was administered to tumor-bearing mice within the tumor vascular window. Dorsal skin fold windows were implanted with LLC tumors and tumor blood vessels developed within the windows over 7 days (see FIG. 13A). Animals were randomly assigned into each of four treatment groups including untreated control, ALX-349 alone, 3 Gy alone, or ALX-349 prior to 3 Gy. ALX-349 (25 mg/kg) was injected i.p. 30 minutes before irradiation. Tumor vascular windows were then treated with superficial x-rays. Tumor blood vessels were quantified by vascular length density (VLD).

FIGS. 13A-13G show that the Akt inhibitor ALX-349 enhanced radiation induced destruction of tumor vasculature. Radiation alone or ALX-349 alone had little effect on established blood vessels. In comparison, mice treated with ALX-349 prior to irradiation had significant vascular regression as compared to ALX-349 alone or radiation alone (P=0.04). Akt inhibition followed by irradiation causes a significant reduction in tumor vascularity to 26% of that measured prior to treatment. In comparison, ALX-349 alone or 3 Gy alone achieved no significant reduction in vascular length density within the dorsal skin fold window model (see FIG. 13A).

To determine whether LiCl attenuates this inducible induction in microvasculature, LiCl was administered prior to therapy. LiCl significantly attenuated the microvasculature destruction resulting in 75% VLD as compared to untreated controls.

Because GSK3β contributes to angiogenesis, the role of GSK3β in radiation-induced capillary tubule formation was investigated. To verify the role of GSK3β signaling during in vivo vascular response, capillary formation was studied in the irradiated mouse utilizing VEGF within MATRIGEL™ Basement Membrane Matrix implanted subcutaneously into the mouse flank. The mouse flank was then irradiated with 3 Gy and FITC-dextran was injected by tail vein 72 hours later. The FITC-dextran containing capillaries within the MATRIGEL™ Basement Membrane Matrix plug were imaged by fluorescence microscopy (see FIGS. 13B-13F). Capillary formation within MATRIGEL™ Basement Membrane Matrix occurred within the irradiated mouse flank. Adenovirus vectors containing dominant negative constructs of Akt and GSK3β were added to the MATRIGEL™ Basement Membrane Matrix at 2×10$^8$ PFU/500 μl. Capillaries were counted by microscopy.

As shown in FIG. 11G, the Akt dominant negative entirely eliminated capillary-like tubule formation. In comparison, the GSK3β dominant negative reversed the effect of the Akt mutant on capillary formation (P=0.04).

Discussion of Examples 8-13

GSK3 Responses to Radiation Therapy in Endothelium

The PI3K/Akt signaling pathway plays a central role in the survival of growth factor-dependent endothelial cells during angiogenesis (Datta et al., 1999). Inhibition of PI3K/Akt-enhanced radiation induced tumor vascular destruction growth factor or PI3K inhibitor has gained significant attention recently (Edwards et al., 2002; Geng et al., 2004; Geng et al., 2001; Tan and Hallahan, 2003). Recent results have shown that overexpression of a dominant negative Akt leads to selective induction of apoptosis in tumor cells.

On the other hand, dominant negative Akt had minimal effect in normal cells (Jetzt et al., 2003). These results are in agreement with other studies using an RNAi technique to inactivate Akt (Liu et al., 2001). As disclosed herein, a dominant negative Akt alone did not significantly induce apoptosis within vascular endothelial cells as compared to untreated controls. On the other hand, overexpression of a dominant negative Akt sensitized vascular endothelial cells to radiation-induced apoptosis. These results support the role of Akt-mediated signal transduction in maintaining endothelial cell viability during irradiation.

Akt signaling participates in angiogenesis following VEGF stimulation of endothelial cells and regulates capillary-like tubule formation (Gerber et al., 1998). Akt can be activated by radiation in absence of growth factor (Edwards et al., 2002; Sonveaux et al., 2003). This observation led to the present investigation to determine whether the biological effects of radiation are mediated through the phosphorylation of Akt downstream targets in endothelial cells. Overexpression of the Akt dominant negative prevented capillary tubule formation. Similarly, Akt inhibitors enhanced radiation-induced destruction of microvasculature within the dorsal skin fold window model. Taken together, these findings demonstrate that Akt contributed to endothelial response to x-irradiation.

Radiation stimulates endothelial cell colonization of MATRIGEL™ Basement Membrane Matrix implanted into mice, where they formed capillary-like structures (Sonveaux et al., 2003). Because GSK3β contributes to angiogenesis (Kim et al., 2002), the role of GSK3β in radiation induced capillary tubule formation was studied. The in vivo formation of new microvasculature was studied in both the dorsal skin fold vascular window and capillary-like tubule formation. Recently, it was reported that activation of GSK3β signaling inhibited the migration of endothelial cell and blocked angiogenesis in an in vivo MATRIGEL™ Basement Membrane Matrix plug assay. Furthermore, inhibition of GSK3β signaling enhanced capillary formation (Kim et al., 2002). These results suggest that GSK3β plays a key role in controlling endothelial cell survival and angiogenesis, similar to the roles previously defined for Akt in endothelial cells (Kim et al., 2002).

As disclosed herein, GSK3β was phosphorylated in response to irradiation, thereby inactivating GSK3. These data are consistent with the premise that the PI3K/Akt signaling pathway is a mediator of GSK3β phosphorylation in response to irradiation and suggest a role for GSK3β in irradiated endothelial cells.

GSK3β is involved in diverse cellular processes, including glycogen synthesis, proliferation, apoptosis, and development (Doble and Woodgett, 2003). Overexpression of a dominant negative GSK3β can protect cells from death induced by deprivation of growth factors or serum starving in neuron (Pap and Cooper, 1998). GSK3β inhibitor lithium can rescue neurons from trophic deprivation (Hongisto et al., 2003). Furthermore, overexpression of constitutively active GSK3β can induce neuronal cell death (Sanchez et al., 2003). To further investigate how dominant negative Akt sensitizes endothelial cells to radiation, the dominant negative GSK3β and lithium were used to block GSK3-mediated signal transduction. The present disclosure demonstrated that GSK3 activation can prevent endothelial cell death induced by combined Akt antagonist and radiation.

The role of GSK3 in regulating cell death is consistent with other reports (Hongisto et al., 2003; Pap and Cooper, 1998).

Although LiCl has non-specific effects (Bijur et al., 2000; Mao et al., 2001), overexpression of a GSK3β dominant negative is a specific way to inhibit this signal transduction pathway (Summers et al., 1999). The present study utilized LiCl to study the mouse model primarily because it is not feasible to utilize the dominant negative genetic construct within the microvascular window model. The contribution of GSK3β signal transduction in the radiation response in endothelium was verified by use of the dominant negative genetic construct within MATRIGEL™ Basement Membrane Matrix placed subcutaneously into the flank of a mouse. These models indicate that the response of microvasculature to radiation can be modified by manipulating GSK3β enzymatic activity. Considering that the response of the microvasculature to ionizing radiation plays a predominant role in the response of normal tissues and tumors to radiotherapy, this signal transduction pathway presents molecular targets for the augmentation of cancer therapy.

All of the compositions and/or methods disclosed and claimed herein can be made and executed without undue experimentation in light of the present disclosure. While the compositions and methods of the presently disclosed subject matter have been described in terms of representative embodiments, it will be apparent to those of skill in the art that variations can be applied to the compositions and/or methods and in the steps and/or in the sequence of steps of the methods described herein without departing from the concept, spirit, and scope of the presently disclosed subject matter. More specifically, it will be apparent that certain agents which are both chemically and physiologically related can be substituted for the agents described herein while the same or similar results would be achieved. All such similar substitutes and modifications apparent to those skilled in the art are deemed to be within the spirit, scope, and concept of the presently disclosed subject matter.

REFERENCES

The references listed below, as well as all references cited in the specification, including but not limited to patents, patent applications, patent application publications, and scientific journal articles, are incorporated herein by reference in their entireties to the extent that they supplement, explain, provide a background for, or teach methodology, techniques, and/or compositions employed herein.

Abayomi, *Acta Oncol.*, 35:659-663, 1996.
Abayomi, *Acta Oncol.*, 41:346-351, 2002.
Baichwal and Sugden, In *Gene Transfer*, Kucherlapati (Ed.), NY, Plenum Press, 117-148, 1986.
Bates, *Mol. Biotechnol.*, 2(2):135-145, 1994.
Battraw and Hall, *Theor. App. Genet.*, 82(2):161-168, 1991.
Bhattacharjee et al., *J. Plant Bioch. Biotech.*, 6(2):69-73. 1997.
Bianco et al., *Oncogene*, 22:2812-2822, 2003.
Bijur and Jope, *J. Neurochem.*, 75:2401-2408, 2000.
Bijur et al., *J. Biol. Chem.*, 275:7583-7590, 2000.
Boyle et al., *Cell*, 64:573-584, 1991.
Brazil and Hemmings, *Trends Biochem. Sci.*, 26:657-664, 2001.
Burgering and Coffer, *Nature*, 376:599-602, 1995.
Chang et al., *Hepatology*, 14:134 A, 1991.
Chen and Chuang, *J. Biol. Chem.*, 274:6039-6042, 1999.
Chen and Okayama, *Mol. Cell. Biol.*, 7(8):2745-2752, 1987.
Chong et al., *Proc. Natl. Acad. Sci. USA*, 97:889-894, 2000.
Christou et al., *Proc. Nat. Acad. Sci. USA*, 84(12):3962-3966, 1987.
Chuang et al., *Bipolar Disord.*, 4:129-136, 2002.
Cimarosti et al., *Neurosci. Lett.*, 315:33-36, 2001.
Clark et al., *Hum. Gene Ther.*, 6(10):1329-1341, 1995.
Coffin, In: *Virology*, Fields et al. (Eds.), Raven Press, NY, 1437-1500, 1990.
Coghlan et al., *Chem Biol* 7:793-803, 2000.
Cohen and Goedert, *Nat Rev Drug Discov* 3:479-87, 2004.
Couch et al., *Am. Rev. Resp. Dis.*, 88:394-403, 1963.
Coupar et al., *Gene*, 68:1-10, 1988.
Crellin et al., *Clin. Oncol.*, 5:5139-142, 1993.
Cross et al., *Nature*, 378(6559):785-789, 1995.
Culbert et al., *FEBS Lett.*, 507:288-294, 2001.
Czurko et al., *Proc. Natl. Acad. Sci. USA*, 94:2766-2771, 1997.
D'Halluin et al., *Plant Cell*, 4(12):1495-1505, 1992.
Datta et al., *Genes Dev.*, 13:2905-2927, 1999.
Doble and Woodgett, *J. Cell Sci.*, 116:1175-1186, 2003.
Dominguez et al., *Proc. Natl. Acad. Sci. USA*, 92(18):8498-8502, 1995.
Edwards et al., *Cancer Res.*, 62:4671-4677, 2002.
Eldar-Finkelman et al., *Proc. Natl. Acad. Sci. USA*, 93:10228-10233, 1996.
European Patent Application No. 0273085
Fechheimer, et al., *Proc. Natl. Acad. Sci. USA*, 84:8463-8467, 1987.
Ferrer et al., *J. Neuropathol. Exp. Neurol.*, 52:370-378, 1993.
Flotte and Carter, *Gene Ther.*, 2(6):357-62, 1995.
Flotte et al., *Am. J. Respir. Cell Mol. Biol.*, 7(3):349-356, 1992.
Flotte et al., *Proc. Natl. Acad. Sci. USA*, 90(22):10613-10617, 1993.
Fraley et al., *Proc. Natl. Acad. Sci. USA*, 76:3348-3352, 1979.
Friedmann, *Science*, 244:1275-1281, 1989.
Garcia-Barros et al., *Science*, 300:1155-1159, 2003.
Geng et al., *Cancer Res.*, 61:2413-2419, 2001.
Geng et al., *Cancer Res.*, 64(14):4893-4899, 2004.
Gerber et al., *J. Biol. Chem.*, 273:30336-30343, 1998.
Ghosh-Choudhury et al., *EMBO J.*, 6:1733-1739, 1987.
Gomez-Foix et al., *J. Biol. Chem.*, 267:25129-25134, 1992.
Gopal, *Mol. Cell. Biol.*, 5:1188-1190, 1985.
Graham and Prevec, *In Methods in Molecular Biology: Gene Transfer and Expression Protocol*, Murray (Ed.), Humana Press, Clifton, N.J., 7:109-128, 1991.
Graham and Van Der Eb, *Virology*, 52:456-467, 1973.
Graham et al, *J. General Virology*, 36:59-74, 1977.
Grimes and Jope, *Prog. Neurobiol.*, 65:391-426, 2001.
Grimes and Jope, *J. Neurochem.*, 78:1219-1232, 2001.
Grunhaus and Horwitz, *Seminar in Virology*, 3:237-252, 1992.
Hall, *In Radiobiology for Radiologist*, 5$^{th}$ Ed., Lippincott Williams and Wilkins, Philadelphia, 5-17, 2000.
Harland and Weintraub, *J. Cell Biol.*, 101(3):1094-1099, 1985.
Harwood et al., *Cell*, 80(1):139-148, 1995.
He et al., *Mol. Cell. Biol.*, 18:6624-6633, 1998.
He et al., *Nature*, 374(6523):617-622, 1995.
He et al., *Plant Cell Reports*, 14 (2-3):192-196, 1994.
Hessdorffer et al., *DNA Cell Biol.*, 9:713-723, 1990.
Herz and Gerard, *Proc. Natl. Acad. Sci. USA*, 90:2812-2816, 1993.
Hetman et al., *J. Neurosci.*, 20:2567-2574, 2000.
Hongisto et al., *Mol. Cell. Biol.*, 23:6027-6036, 2003.
Hongisto et al., *Mol. Cell. Biol.*, 23:6027-6036, 2003.
Horwich et al. *J. Virol.*, 64:642-650, 1990.
Hou and Lin, *Plant Physiology*, 111:166, 1996.
Inouye et al., *J. Radiat. Res. (Tokyo)*, 36:203-208, 1995.
Jannoun and Bloom, *Int. J. Radiat. Oncol. Biol. Phys.*, 18:747-753, 1990.

Jetzt et al., *Cancer Res.*, 63:6697-6706, 2003.
Jones and Shenk, *Cell*, 13:181-188, 1978.
Jope, *Trends Pharmacol. Sci.*, 24:441-443, 2003.
Jurgensmeier et al., *Proc. Natl. Acad. Sci. USA*, 95:4997-5002, 1998.
Kaeppler et al., *Plant Cell Reports*, 9:415-418, 1990.
Kaneda et al., *Science*, 243:375-378, 1989.
Karlsson et al., *EMBO J.*, 5:2377-2385, 1986.
Kasahara et al., *Science*, 266(5189):1373-1376, 1994.
Kato et al, *J. Biol. Chem.*, 266:3361-3364, 1991.
Kim et al., *J. Biol. Chem.*, 277:41888-41896, 2002.
Klein and Melton, *Proc. Natl. Acad. Sci. USA*, 93:8455-8459, 1996.
Kotani et al., *J. Biol. Chem.*, 274:21305-21312, 1999.
Kotin et al., *Proc. Nat. Acad. Sci. USA*, 87(6):2211-2215, 1990.
LaFace et al., *Virology*, 162(2):483-486, 1988.
Laughlin et al., *J. Virol.*, 60(2):515-524, 1986.
Lawlor and Alessi, *J. Cell Sci.*, 114:2903-2910, 20011.
Lazzeri, *Methods Mol Biol*, 49:95-106, 1995.
Le Gal La Salle et al., *Science*, 259:988-990, 1993.
Lebkowski et al., *Mol. Cell. Biol.*, 8(10):3988-3996, 1988.
Lee et al., *Environ. Mol. Mutagen.*, 13(1):54-59, 1989.
Lessell, *J. Neuroopthalmol.*, 24(3):243-250, 2004.
Levrero et al., *Gene*, 101:195-202, 1991.
Liu et al., *J. Exp. Med.*, 194:113-126, 2001.
Luo et al., *J. Clin. Invest.*, 106:493-9, 2000.
Madsen et al., *Neuroscience*, 119:635-642, 2003.
Mandriota and Pepper, *J. Cell Sci.*, 110(Pt 18):2293-2302, 1997.
Mann et al., *Cell*, 33:153-159, 1983.
Mao et al., *J. Biol. Chem.*, 276:26180-26188, 2001.
Markowitz et al., *J. Virol.*, 62:1120-1124, 1988.
Mazure et al., *Blood*, 90:3322-3331, 1997.
McCarty et al., *J. Virol.*, 65(6):2936-2945, 1991.
McLaughlin et al., *J. Virol.*, 62(6):1963-1973, 1988.
Meadows et al., *Lancet*, 2:1015-1018, 1981.
Miller et al., *Am. J. Clin. Oncol.*, 15(3):216-221, 1992.
Mizumatsu et al., *Cancer Res.*, 63:4021-4027, 2003.
Monje et al., *Nat. Med.*, 8:955-962, 2002.
Muzyczka, *Curr. Topics Microbiol. Immunol.*, 158:97-129, 1992.
Nabel et al., *Science*, 244(4910):1342-1344, 1989.
Nagai et al., *Surg. Neurol.*, 53:503-506, 2000.
Nicolas and Rubenstein, In *Vectors: A Survey of Molecular Cloning Vectors and Their Uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Nonaka and Chuang, *Neuroreport.*, 9:2081-2084, 1998.
Nonaka et al., *Proc. Natl. Acad. Sci. USA*, 95:2642-2647, 1998.
Ohi et al., *Gene*, 89(2):279-282, 1990.
Oltvai et al., *Cell*, 74:609-619, 1993.
Omirulleh et al., *Plant Mol. Biol.*, 21(3):415-28, 1993.
Pap and Cooper, *J. Biol. Chem.*, 273:19929-19932, 1998.
Pap and Cooper, *J. Biol. Chem.*, 273:19929-19932, 1998.
Pap and Cooper, *Mol. Cell. Biol.*, 22:578-586, 2002.
Paris et al., *Science*, 293:293-297, 2001.
Paskind et al., *Virology*, 67:242-248, 1975.
PCT Appln. WO 9217598
PCT Appln. WO 94/09699
PCT Appln. WO 95/06128
Peissner et al., *Brain Res. Mol. Brain. Res.*, 71:61-68, 1999.
Perales et al., *Proc. Natl. Acad. Sci. USA*, 91:4086-4090, 1994.
Pierce et al., *Development*, 121 (3):755-765, 1995.
Potrykus et al., *Mol. Gen. Genet.*, 199:183-188, 1985.
Potter et al., *Proc. Natl. Acad. Sci USA*, 81:7161-7165, 1984.
Pui et al., *N. Engl. J. Med.*, 349:640-649, 2003.
Racher et al., *Biotechnology Techniques*, 9:169-174, 1995.
Ragot et al., *Nature*, 361:647-650, 1993.
*Remington's Pharmaceutical Sciences*, 18th Ed. Mack Printing Company, 1289-1329, 1990.
Renan, *Radiother. Oncol.*, 19:197-218, 1990.
Rhodes et al., *Methods Mol. Biol.*, 55:121-131, 1995.
Rich et al., *Hum. Gene Ther.*, 4:461-476, 1993.
Ridgeway, In *Vectors: A Survey of Molecular Cloning Vectors and Their Uses*, Rodriguez and Denhardt (Eds.), Stoneham:Butterworth, 467-492, 1988.
Rippe et al., *Mol. Cell. Biol.*, 10:689-695, 1990.
Robison et al., *Am. J. Pediatr. Hematol. Oncol.*, 6:115-121, 1984.
Roman and Sperduto, *Int. J. Radiat. Oncol. Biol. Phys.*, 31:983-998, 1995.
Rosenfeld et al., *Science*, 252:431-434, 1991.
Rosenfeld, et al., *Cell*, 68:143-155, 1992.
Rossig et al., *J. Biol. Chem.*, 277:9684-9689, 2002.
Roux et al., *Proc. Natl. Acad. Sci. USA*, 86:9079-9083, 1989.
Salas et al., *J. Biol. Chem.*, 278:41338-41346, 2003.
Samulski et al., *EMBO J.*, 10:3941-3950, 1991.
Sanchez et al., *Mol. Cell. Biol.*, 23:4649-4662, 2003.
Schueneman et al., *Cancer Res.*, 63:4009-4016, 2003.
Schulz et al., *Curr. Oncol. Rep.*, 3:179-184, 2001.
Schwabe and Brenner, *Am. J. Physiol. Gastrointest. Liver Physiol.*, 283:G204-211, 2002.
Shelling and Smith, *Gene Therapy*, 1:165-169, 1994.
Sigfried et al., *Cell*, 1167-1179, 1992.
Silverman et al., *Cancer*, 54:825-829, 1984.
Sonveaux et al., *Cancer Res.*, 63:1012-1019, 2003.
Stratford-Perricaudet and Perricaudet, In *Human Gene Transfer*, Eds, Cohen-Haguenauer and Boiron, John Libbey Eurotext, France, 51-61, 1991.
Stratford-Perricaudet et al., *Hum. Gene. Ther.*, 1:241-256, 1991.
Summers et al., *J. Biol. Chem.*, 274:17934-17940, 1999.
Tada et al., *Neuroscience*, 99:33-41, 2000.
Takashima et al., *Proc. Natl. Acad. Sci. USA*, 90:7789-7793, 1993.
Tan and Hallahan, *Cancer Res.*, 63:7663-7667, 2003.
Temin, In *Gene Transfer*, Kucherlapati (Ed.), NY, Plenum Press, 149-188, 1986.
Testa and Bellacosa, *Proc. Natl. Acad. Sci. USA*, 98:10983-10985, 2001.
Tong et al., *Eur. J. Neurosci.*, 13:1913-1922, 2001.
Top et al., *J. Infect. Dis.*, 124:155-160, 1971.
Tratschin et al., *Mol. Cell. Biol.*, 4:2072-2081, 1984.
Tsukada et al., *Plant Cell Physiol.*, 30(4)599-604, 1989.
Tur-Kaspa et al., *Mol. Cell. Biol.*, 6:716-718, 1986.
U.S. Pat. Nos. 4,684,611; 4,797,368; 4,952,500; 5,139,941; 5,302,523; 5,322,783; 5,384,253; 5,384,253; 5,384,253; 5,464,765; 5,538,877; 5,538,880; 5,550,318; 5,563,055; 5,563,055; 5,580,859; 5,589,466; 5,591,616; 5,610,042; 5,656,610; 5,670,488; 5,702,932; 5,736,524; 5,780,448; 5,789,215; 5,945,100; 5,981,274; and 5,994,624.
Vivanco and Sawyers, *Nat. Rev. Cancer*, 2:489-501, 2002.
Walsh et al., *J. Clin. Invest*, 94:1440-1448, 1994.
Watcharasit et al., *Proc. Natl. Acad. Sc. USA*, 99:7951-7955, 2002.
Wei et al., *Gene Therapy*, 1:261-268, 1994.
Welsh et al., *Trends Cell Biol.*, 274-279, 1966.
Wilson et al., *Science*, 244:1344-1346, 1989.
Wong et al., *Gene*, 10:87-94, 1980.

Wu and Wu, *Adv. Drug Delivery Rev.*, 12:159-167, 1993.
Wu and Wu, *Biochemistry*, 27:887-892, 1988.
Wu and Wu, *J. Biol. Chem.*, 262:4429-4432, 1987.
Yang et al., *J. Virol.*, 68:4847-4856, 1994.
Zhou et al., *Exp. Hematol*, 21:928-933, 1993.

It will be understood that various details of the presently described subject matter can be changed without departing from the scope of the presently described subject matter. Furthermore, the foregoing description is for the purpose of illustration only, and not for the purpose of limitation.

What is claimed is:

1. A method for treating a hyperproliferative disease in a subject comprising administering radiation therapy in combination with a pharmaceutical composition comprising an inhibitor of glycogen synthase kinase 3 (GSK3) comprising lithium or a pharmaceutically acceptable salt thereof to the subject, wherein the inhibitor of GSK3 is administered to the subject prior to and during administration of the radiation therapy, and in an amount and via a route effective to protect a cell selected from the group consisting of a neuron, a vascular endothelial cell, a salivary gland cell, a gastrointestinal tract cell, a lung cell, and a liver cell from radiation-induced apoptosis.

2. The method of claim 1, wherein the subject is a mammal.

3. The method of claim 2, wherein the mammal is a human.

4. The method of claim 1, wherein the GSK3 inhibitor is administered in a pharmaceutically acceptable carrier, diluent, or vehicle.

5. The method of claim 1, wherein the GSK3 inhibitor is administered to the subject intranasally, intradermally, intraarterially, intraperitoneally, intralesionally, intracranially, intraarticularly, intraprostaticaly, intrapleurally, intratracheally, intravitreally, intravaginally, intrarectally, topically, intratumorally, intramuscularly, intraperitoneally, subcutaneously, subconjunctivally, intravesicularlly, mucosally, intrapericardially, intraumbilically, intraocularally, orally, locally, via inhalation, via injection, via infusion, via continuous infusion, via localized perfusion to a tumor, by bathing target cells directly, via a catheter, via a lavage, in a creme, in a lipid composition, or by any combination of the forgoing.

6. The method of claim 5, wherein the tumor comprises a cancerous tumor.

7. The method of claim 6, wherein the tumor comprises a brain tumor.

8. The method of claim 6, wherein the tumor comprises a lung tumor.

9. The method of claim 1, wherein the hyperproliferative disease is selected from the group consisting of a benign tumor, an arteriovenous malformation, a neuroma, a meningioma, a schwanoma, an adenoma, a glioma, and combinations thereof.

10. The method of claim 9, wherein the neuroma comprises an acoustic neuroma or an optic neuroma.

11. The method of claim 9, wherein the adenoma comprises a pituitary adenoma.

12. The method of claim 9, wherein the glioma comprises an optic glioma.

13. The method of claim 9, wherein the benign tumor is selected from the group consisting of a brain tumor, a spinal cord tumor, an eye tumor, and a lung tumor.

14. The method of claim 1, wherein the hyperproliferative disease comprises cancer.

15. The method of claim 14, wherein the cancer is selected from the group consisting of lung cancer, prostate cancer, ovarian cancer, testicular cancer, brain cancer, skin cancer, colon cancer, gastric cancer, esophageal cancer, tracheal cancer, head and neck cancer, pancreatic cancer, liver cancer, breast cancer, ovarian cancer, lymphoid cancer, leukemia, cervical cancer, vulvar cancer, and cancer of the eye.

16. The method of claim 15, wherein the cancer comprises brain cancer.

17. The method of claim 15, wherein the cancer comprises lung cancer.

18. The method of claim 14, wherein the radiation therapy comprises cranial radiation therapy.

19. The method of claim 14, wherein the administering comprises administering a sufficient amount of the GSK3 inhibitor to result in a reduction in toxicity associated with the radiation therapy to a neuron.

20. The method of claim 19, wherein the neuron comprises a neuron of the central nervous system.

21. The method of claim 20, wherein the neuron is a hippocampal neuron.

22. The method of claim 19, wherein the neuron comprises a neuron of the peripheral nervous system.

23. The method of claim 19, wherein the toxicity comprises neuron death.

24. The method of claim 19, wherein the toxicity comprises apoptosis.

25. The method of claim 18, wherein the administering comprises administering a sufficient amount of the GSK3 inhibitor to result in a reduction in cognitive decline of the subject associated with the cranial radiation therapy.

26. The method of claim 18, wherein the administering comprises a sufficient amount of the GSK3 inhibitor to result in a reduction in toxicity associated with the cranial radiation therapy to non-neuronal cells.

27. The method of claim 26, wherein the non-neuronal cells are vascular endothelial cells.

28. The method of claim 26, wherein the non-neuronal cells are salivary gland cells, gastrointestinal tract cells, lung cells, liver cells, or vascular endothelial cells.

29. The method of claim 28, wherein the toxicity comprises death of the cells.

30. The method of claim 28, wherein the toxicity comprises apoptosis of the cells.

31. The method of claim 28, wherein the reduction of toxicity comprises an elimination of toxicity.

32. The method of claim 1, further comprising administering a second pharmaceutical composition.

33. The method of claim 32, wherein the second pharmaceutical composition comprises an anti-cancer composition.

34. The method of claim 1, wherein the inhibitor of GSK3 is administered to the subject beginning about 7 days prior to the administration of the radiation therapy.

35. The method of claim 34, wherein the inhibitor of GSK3 is administered daily to the subject beginning about 7 days prior to the administration of the radiation therapy.

* * * * *

UNITED STATES PATENT AND TRADEMARK OFFICE
CERTIFICATE OF CORRECTION

PATENT NO. : 8,771,754 B2
APPLICATION NO. : 11/663314
DATED : July 8, 2014
INVENTOR(S) : Dennis Hallahan Page 1 of 1

It is certified that error appears in the above-identified patent and that said Letters Patent is hereby corrected as shown below:

IN THE SPECIFICATION:

Col. 1, Line 14 GRANT STATEMENT
  replace "This work was supported by grants, R01-CA89674, P30-CA68485, R01-CA112385, R01-CA88076, and P50-CA90949 from the National Institutes of Health, P50-CA90949 from the Vanderbilt Lung Cancer SPORE, and CCSG P30-CA68485 from the Vanderbilt-Ingram Cancer Center. Thus, the U.S. government has certain rights in the presently disclosed subject matter."
  with --This invention was made with government support under Grant Nos. R01-CA58508, R01-CA70937, R01-CA89674, R01-CA89888, R01-CA068485, R01-CA90949, R01-CA112385, and R01-CA088076 from the National Institutes of Health. The government has certain rights in the invention.--

Signed and Sealed this
Eighteenth Day of November, 2014

Michelle K. Lee
*Deputy Director of the United States Patent and Trademark Office*